(12) United States Patent
Dickerson et al.

(10) Patent No.: US 11,142,776 B2
(45) Date of Patent: Oct. 12, 2021

(54) DELIVERY OF BIOMOLECULES INTO CELLS THROUGH CARBON NANOTUBE ARRAYS

(71) Applicants: UNIVERSITY OF ROCHESTER, Rochester, NY (US); ROCHESTER INSTITUTE OF TECHNOLOGY, Rochester, NY (US); Ian Dickerson, Pittsford, NY (US); Michael Schrlau, Pittsford, NY (US); Masoud Golshadi, Ithaca, NY (US)

(72) Inventors: Ian Dickerson, Pittsford, NY (US); Michael Schrlau, Pittsford, NY (US); Masoud Golshadi, Ithaca, NY (US)

(73) Assignees: UNIVERSITY OF ROCHESTER, Rochester, NY (US); ROCHESTER INSTITUTE OF TECHNOLOGY, Rochester, NY (US)

( * ) Notice: Subject to any disclaimer, the term of this patent is extended or adjusted under 35 U.S.C. 154(b) by 491 days.

(21) Appl. No.: 15/764,020

(22) PCT Filed: Sep. 30, 2016

(86) PCT No.: PCT/US2016/054743
§ 371 (c)(1),
(2) Date: Mar. 28, 2018

(87) PCT Pub. No.: WO2017/059230
PCT Pub. Date: Apr. 6, 2017

(65) Prior Publication Data
US 2018/0273978 A1    Sep. 27, 2018

Related U.S. Application Data

(60) Provisional application No. 62/235,386, filed on Sep. 30, 2015.

(51) Int. Cl.
*C12N 15/89* (2006.01)
*B01L 3/00* (2006.01)
(Continued)

(52) U.S. Cl.
CPC ............ *C12N 15/89* (2013.01); *B01L 3/0293* (2013.01); *B01L 3/502* (2013.01); *C12N 5/0075* (2013.01);
(Continued)

(58) Field of Classification Search
CPC ...... C12N 15/89; C12N 15/87; C12N 5/0075; B01L 2300/0838; B01L 2300/896;
(Continued)

(56) References Cited

U.S. PATENT DOCUMENTS

2012/0276573 A1* 11/2012 VanDersarl .......... C12N 5/0075
435/29

OTHER PUBLICATIONS

M. Golshadi et al.: "Template-Based Synthesis of Aligned Carbon Nanotube Arrays for Microfluidic and Nanofluidic Applications", ECS Transactions, vol. 50, No. 33, May 10, 2013 (May 10, 2013), pp. 1-14. (Year: 2003).*
(Continued)

*Primary Examiner* — Michael L Hobbs
(74) *Attorney, Agent, or Firm* — Meunier Carlin & Curfman LLC

(57) ABSTRACT

Disclosed herein are carbon nanotube arrays as well as transfer systems comprising said carbon nanotube arrays and an administration platform. The disclosed carbon nanotube arrays can also be provided in kits further comprising a culture platform. Also disclosed herein is the use of said carbon nanotube arrays and transfer systems in administering agents to a cell.

21 Claims, 11 Drawing Sheets

(51) Int. Cl.
    *B01L 3/02*       (2006.01)
    *C12N 5/00*      (2006.01)
    *B82Y 5/00*       (2011.01)
    *B82Y 40/00*     (2011.01)
    *C12N 15/87*    (2006.01)
    *C01B 32/158*   (2017.01)

(52) U.S. Cl.
    CPC ......... *B01L 2300/0838* (2013.01); *B01L 2300/0896* (2013.01); *B01L 2400/0406* (2013.01); *B82Y 5/00* (2013.01); *B82Y 40/00* (2013.01); *C01B 32/158* (2017.08); *C12N 15/87* (2013.01)

(58) Field of Classification Search
    CPC ... B01L 2400/0406; B82Y 40/00; B82Y 5/00; C10B 32/158
    See application file for complete search history.

(56) References Cited

OTHER PUBLICATIONS

Persson, H. et al. "Vertical oxide nanotubes connected by subsurface microchannels", Nano Research, vol. 5, No. 3, Feb. 7, 2012, pp. 190-198.

Peer, E. et al. "Hollow Nanoneedle Array and Its Utilization for Repeated Administration of Biomolecules to the Same Cells", ACS NANO, vol. 6, No. 6, Jun. 26, 2012, pp. 4940-4946.

Skold, N. et al. "Nanofluidic in hollow nanowires", Nanotechnology, vol. 21, No. 15, Apr. 16, 2010, p. 155301.

International Search Report and Written Opinion dated Feb. 8, 2017, from International Application No. PCT/US2016/054743, 10 pages.

Golshadi, M. et al. "Template-Based Synthesis of Aligned Carbon Nanotube Arrays for Microfluidic and Nanofluidic Applications", ECS Transactions, 50 (33) 1-14 (2013).

* cited by examiner

FIG. 4
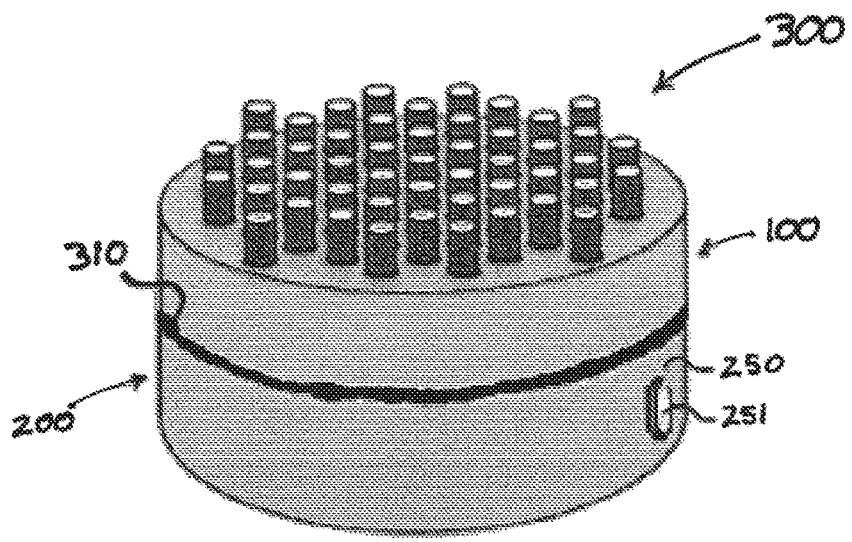
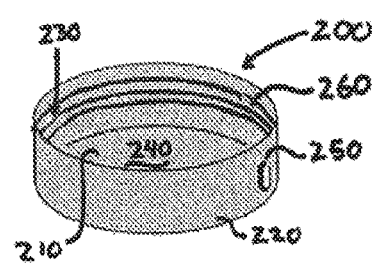
FIG. 5a
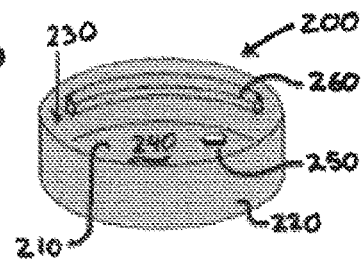
FIG. 5b
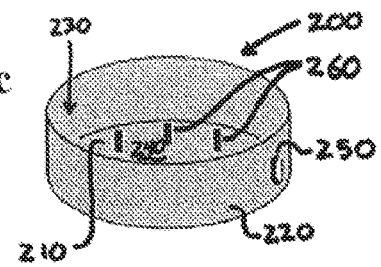
FIG. 5c

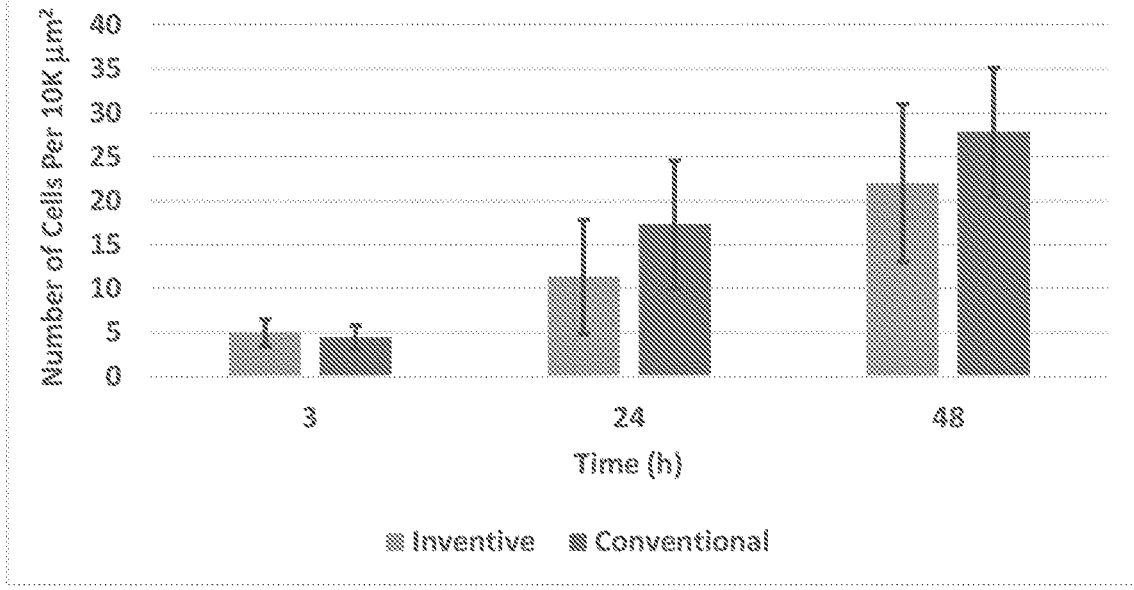
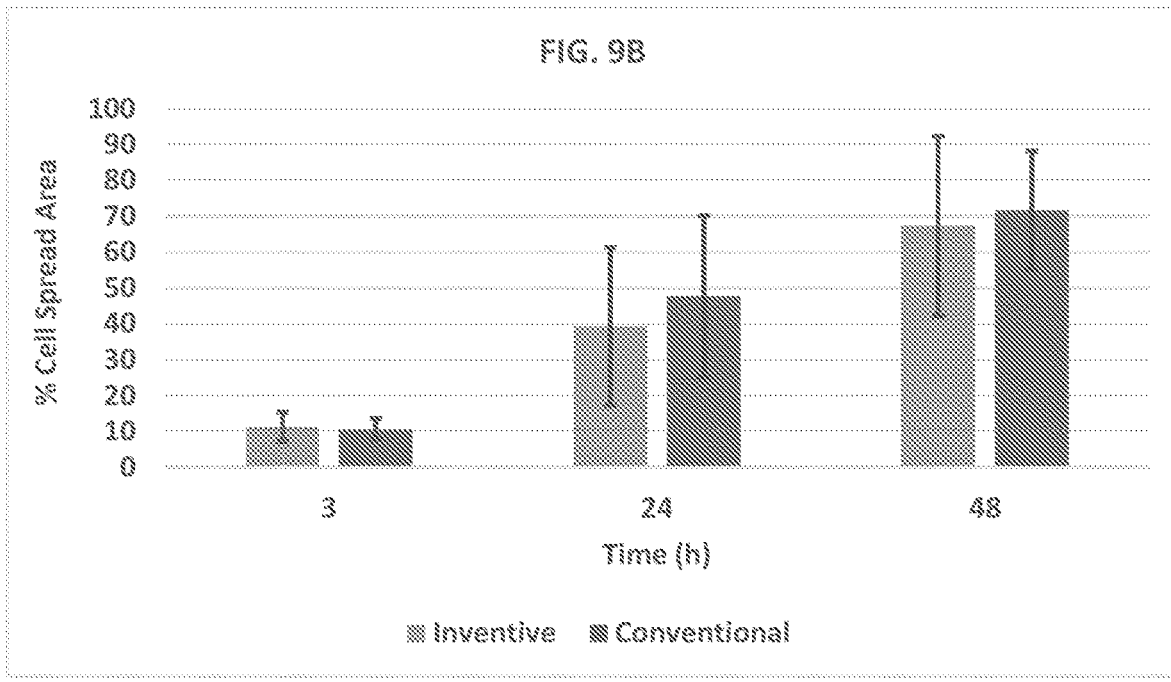

DELIVERY OF BIOMOLECULES INTO CELLS THROUGH CARBON NANOTUBE ARRAYS

FIELD OF THE INVENTION

The present invention relates to an apparatus and method for intracellular delivery of biomolecules. In particular, the present invention is directed to a carbon nanotube array for delivery of biomolecules into cellular bodies; the fabrication of the same.

BACKGROUND OF THE INVENTION

The study of cellular physiology is key to modern molecular medicine and the continued development of medical technologies. At present, cellular physiology is commonly studied through the transfer of biomolecules into target cells followed by culture and observation of the target cells to study resultant cellular morphologies.

Transfer of agents 700 (including, but not limited to macromolecules, nanoparticles, nucleic acids and pharmaceuticals) into target cells is thus a fundamental tool in the study of cellular biochemistry, in the development of transgenic models, and in the manipulation of target cells. At the same time, however, the task of transferring agents into target cells having physiologic characteristics representative of in vivo physiology presents a limiting step in the study of cellular physiology and pathophysiology. While immortalized cell lines are excellent equivalents of "living test-tubes" for establishing basic cellular biology, they are not true representatives of in vivo conditions, having under gone the immortalization/transformation process and being grown in conditions where cells are typically missing endocrine and neuronal input of tissue environment. In contrast, primary cells more closely represent in vivo conditions, and if co-cultured with appropriate cells, can begin to represent the nuances of the rich cellular environment found in vivo. However, introduction of nucleic acids into primary cells is currently inefficient requiring harsh conditions or construction of complex viral vectors, and is time consuming.

Conventional methods for the intracellular delivery of agents (such as nucleic acids and small molecule pharmaceuticals) include lipofection; electroporation; viral vectors; biolistics (e.g., a gene gun); and microinjection of individual cells. However, each of these methods has undesirable limitations. For example, lipofection can have high toxicity and low efficiency, particularly for post-mitotic cells; electroporation requires significant investment in hardware and has variable efficiency and significant toxicity; many cell types cannot be consistently transfected by lipofection or electroporation (e.g., stem cells, primary cells, induced pluripotent stem cells (iPSCs), immune T-cells); viral vectors are labor-intensive to construct and can have high toxicity at high titers (necessary for increased efficiency) and have a limited packing size, thus limiting the types of experiments that can be undertaken; biolistics requires expensive hardware and has low efficiency and high toxicity; and microinjection has low transfection rates dictated by single-cell injection, which is very time-consuming and has significant toxicity resulting from physical damage to the cells.

To overcome the foregoing limitations of conventional agent transfer methods, transfer by physical structures has been investigated, using either solid rods or hollow tubes to deliver genetic material to target cells. To this end, two main device platforms consisting of single or array of nanostructures have been developed. In particular, attempts have been made to coat single-tip devices such as nanowires, silicon rods or carbon nanopipettes, with agents such as plasmid DNA to target cells by physical contact. However, these single-tipped devices have been inefficient, because of low transfection rate due to serial approach of nanoinjection, and incapability of probing multiple cells in parallel, making the process time-consuming, and resulting in significant toxicity from physical damage to the cells. As a result single-tipped nanodevices have limited qualitative and quantitative abilities when analyzing populations of cells.

To overcome the limitations of single-tipped tools for parallel injection, devices have been fabricated with arrays of nanostructures. It is thought that such nanostructures, by foregoing chemical or biological reagents, may increase transfer loads while lowering cellular toxicity. Vertically aligned silicon nanowires have been employed as a delivery tool by attaching the biomolecules to the nanowires. Also, an array of carbon nanotubes (CNTs) has been used for intracellular delivery of plasmid and nanoparticles, in which the inner lumen of CNTs was employed as a reservoir for loading targeted biomolecules for delivery. However, there remains a number of limitations in the use of such platforms. For example, they require long incubation times and tend to distort cellular membranes and inhibit subsequent removal of target cells, thereby precluding further post-injection processing of target cells (e.g., re-culturing of injected cells). Furthermore, because the nucleic acid must be first coated on the nanowire before cells are plated onto the device, the final concentration and the time of application cannot be precisely controlled.

Further attempts have employed nanotubes constructed of open-ended alumina to transfer agents directly into target cells. Alumina nanotube platforms employ an array of tall nanotubes (>1 μm) randomly distributed at low density, resulting in 10-70 tubes per cell. However, nanotube platforms constructed with alumina tubes have had low efficiency for gene transfer when using passive mechanism, and required electroporation to achieve higher efficiency (70%), but suffered from limitations associated with electroporation as described above. Electroporation increases cost, complexity and cytotoxicity, thereby decreasing overall efficiency.

Accordingly, there remains a need in the art for an intracellular transfer method that enables high transfer efficiency with low cellular toxicity. Preferably, such a transfer method will enable intracellular delivery of a variety of different agent types to large populations of cells, including cell populations composed of multiple target cell varieties, while facilitating post-injection growth of target cells. It is also preferable that such a method be minimally invasive so as to not distort cellular membranes, and thereby promote subsequent handling of injected cells for further post-injection processing.

SUMMARY OF THE INVENTION

In one embodiment, disclosed herein are carbon nanotube (CNT) arrays, comprising hollow carbon nanotubes arranged on a base; wherein the base comprises a first planar surface and a second planar surface; wherein the hollow carbon nanotubes extend from the first planar surface to the second planar surface, and comprise first open ports at the first planar surface and second open ports at the second planar surface; wherein the first open ports are inlet ports and the second open ports are outlet ports, and a fluid flow passage channel extends between pairs of inlet and outlet ports such that there is a fluidic communication between the first planar surface and the second planar surface of the base via the hollow carbon nanotubes; wherein the hollow carbon nanotubes comprise nanotubes having a diameter from about 150 nm to about 200 nm; wherein the hollow carbon nanotubes comprises nanotubes arranged 0.2 µm to 0.5 µm center-to-center spacing resulting in approximately 1000 tubes per cell; wherein substantially all nanotubes in the CNT array extend no further than about 0.3 µm beyond the second planar surface of the base; and wherein the hollow carbon nanotubes have a configuration that enables support of a cell thereon without compromising the cell health or cell morphology.

Also disclosed are CNT transfer systems, comprising:
a CNT array according to any preceding embodiment; and
an administration platform;
wherein the administration platform comprises an open end and a closed end, the open end having an opening dimensioned to accommodate placement of the CNT array inside the administration platform; and wherein the administration platform comprises one or more support surfaces for supporting the CNT array and preventing the CNT array from contacting the closed end.

Also disclosed are CNT transfer systems, comprising:
a CNT array according to any preceding embodiment; and
an administration platform;
wherein the administration platform comprises two open ends, with at least a first of the two open ends being dimensioned to accommodate placement of the CNT array inside the administration platform; wherein the second of the two open ends has a perimeter edge suitable for sealing with a planar surface of a tissue culture dish; and wherein the administration platform comprises one or more support surfaces that for supporting the CNT array and preventing the CNT array from contacting the planar surface of the tissue culture dish.

Also disclosed are CNT transfer kits for administering an agent into a cell, comprising: a CNT array according to any preceding embodiment; and a culture platform.

In one embodiment, also disclosed are methods of administering an agent into a cell with a carbon nanotube (CNT) array, comprising:
contacting the cell with a CNT array according to any preceding embodiment;
wherein the cell is placed in contact with the second planar surface of the base of the CNT array; wherein the CNT array supports the cell without compromising the cell health or cell morphology; and wherein the agent is administered to the first planar surface of the base in a manner allowing flow of the agent into the inlet ports, through the fluid passage channels, and out the outlet ports of the CNT array so as to come into contact with the cell supported on the CNT array.

In one embodiment, disclosed herein are methods of making a carbon nanotube (CNT) array comprising
a. depositing carbon on a porous anodized aluminum oxide (AAO) membrane by chemical vapor deposition; wherein the deposited carbon coats an entire surface of the AAO membrane, including internal surfaces of pores in the AAO membrane;
b. removing deposited carbon on one side of the AAO membrane by oxygen plasma etching;
c. exposing an array of hollow carbon nanotubes by using reactive ion etching with boron trichloride gas to selectively remove the AAO membrane on the same side that deposited carbon was removed in step (b), exposing carbon nanotubes that were formed in the membrane pore.

Both the foregoing general description and the following detailed description are exemplary and explanatory only and are intended to provide further explanation of the invention as claimed. The accompanying drawings are included to provide a further understanding of the invention; are incorporated in and constitute part of this specification; illustrate embodiments of the invention; and, together with the description, serve to explain the principles of the invention.

BRIEF DESCRIPTION OF THE DRAWINGS

Further features and advantages of the invention can be ascertained from the following detailed description that is provided in connection with the drawings described below:

FIG. 4 shows a CNT transfer system using the CNT array shown in FIG. 1;

FIG. 5a shows a first example of an administration platform for use in the CNT transfer system shown in FIG. 4;

FIG. 5b shows a second example of an administration platform for use in the CNT transfer system shown in FIG. 4;

FIG. 5c shows a third example of an administration platform for use in the CNT transfer system shown in FIG. 4;

FIG. 9a shows number of cells grown on top of a CNT array such as that shown in FIG. 1;

FIG. 9b shows spreading percentage of cells grown on top of a CNT array such as that shown in FIG. 1;

FIG. 11a shows magnified fluorescent images of five HEK293 cells during transfection, showing the live cells stained by calcein-AM dye imaged by GFP fluorescent filter at t=0 min, and FIG. 11b shows the same cells during the CNT-mediated transfection of 10 µM tetramethylrhodamine (dextran) imaged by Cy3 fluorescent filter at t=0, 7, and 16 min (scale bar: 5 µm). The background fluorescence is due to diffusion of dextran into the growth medium through open CNTs (with no cells blocking the exit opening).

FIG. 12a shows the Brightfield image of HEK293 cells cultured on culture plate for 48 hrs before introduction of dextran. FIG. 12b shows fluorescent image of cells incubated in 10 μM solution of dextran (dark spots indicate untransfected cells) after 20 min. FIG. 12c shows fluorescent image of the same cells after rinsing with PBS indicating impermeability of dextran (scale bars: 50 μm).

FIG. 13 shows (a) Fluorescent images of live HEK293 cells cultured on CNT array for 48 hrs and stained with calcein-AM dye imaged by GFP fluorescent filter, (b) cells during the transfection with Qdots (white arrows show the free floating Qdots), and (c) same cells trypsinized and re-cultured in culture plate for 5 hrs after transfection (scale bar: 20 μm). The bright punctuate green transfected Qdots are detectable on a uniform background of calcein-AM staining.

FIG. 14 shows a) L6 cells plated on CNT array and stained with 2 μM calcein-AM dye, and b) transfected with 75 μM propidiumiodide after 14 min, and c) combined fluorescent image of (a) and (b) (scale bar: 200 μm). d) Flow cytometry results of L6 cells transfected with propidium iodide using CNT array device. Transfection indicated by rightward shift in the 670 nm fluorescence intensity of injected cell population (red) compared to control uninjected (blue) cells. 9000 cells were counted for each sample population.

FIG. 15 shows a) Phase image of HEK293 cells, and b) fluorescent images of transfected cells with EYFP plasmid DNA, 48 hrs after transfection, and c) the combined phase and fluorescent image of (a) and (b) (scale bar: 100 μm). d) Flow cytometry results of HEK293 cells transfected with plasmid DNA encoding EYFP by CNT array device. Transfection indicated by rightward shift in the 530 nm fluorescence intensity of injected cell population (red) compared to control uninjected (blue) cells. 25,000 cells were counted for each sample population.

DETAILED DESCRIPTION OF THE INVENTION

The following disclosure discusses the present invention with reference to the examples shown in the accompanying drawings, though does not limit the invention to those examples.

The present invention is directed to a carbon nanotube (CNT) array, a CNT transfer system; methods of assembling a CNT array and a CNT transfer system incorporating a CNT array; and methods of transferring materials into cells via hollow carbon nanotubes (CNTs).

Figure 1:
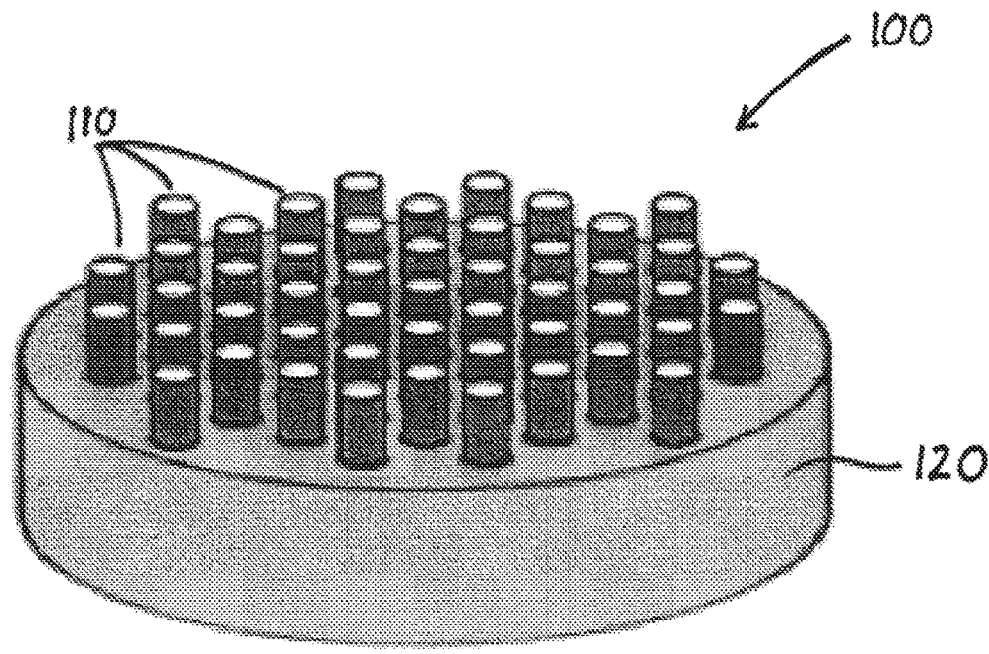
FIG. 1 is an elevated perspective view of a carbon nanotube (CNT) array according to the present invention.
Figure 2:
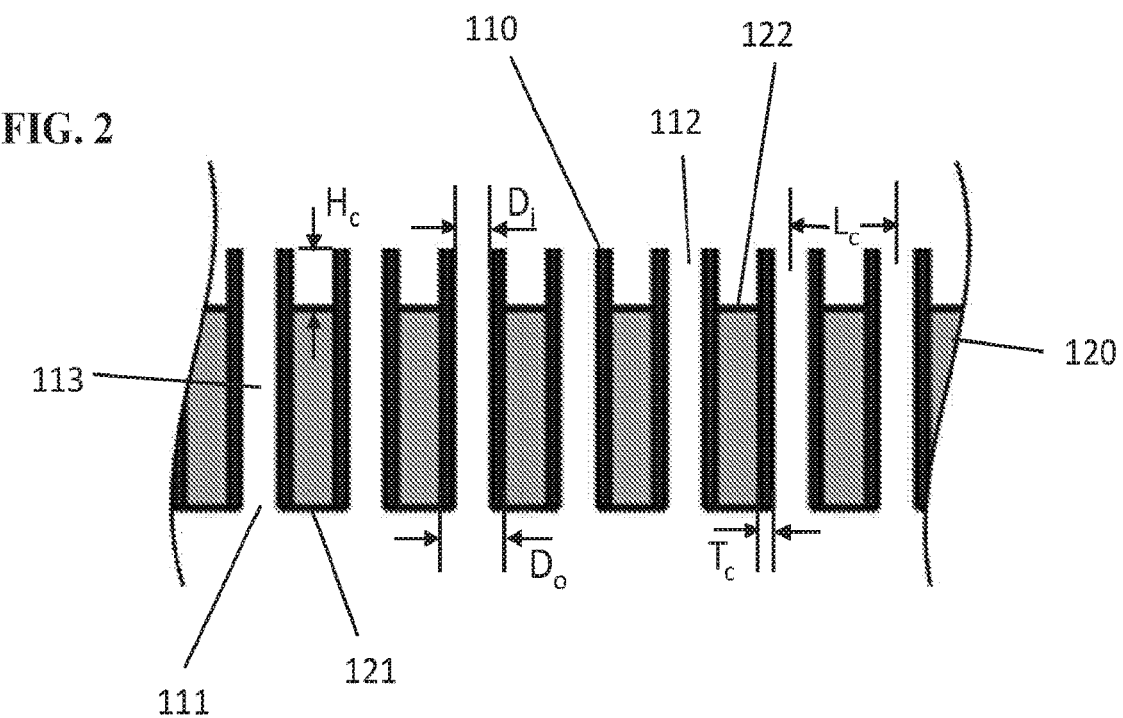
FIG. 2 is a cross-sectional view of the CNT array shown in FIG. 1.

The use of carbon nanotube arrays has proven to be an exciting new method to deliver biomolecules into a cell. However, given the deficiencies of presently available CNT arrays such as poor transfer efficiency and cell distortion, new CNT arrays are needed that do not suffer from these deficiencies. In one aspect, disclosed herein are CNT arrays. FIG. 1 shows one example of a CNT array 100 according to the present invention. The CNT array 100 includes a plurality of CNTs 110 protruding from a substrate base 120. As shown in FIG. 2, individual CNTs 110 extend through the substrate base 120, and include: a first port 111 at an end fixed within the substrate base 120, and opened at a first planar surface 121 of the substrate base 120; a second port 112 at an end protruding from a second planar surface 122 of the substrate base 120; and a hollow passage channel 113 extending through the CNT 110, so as to provide a fluidic communication passage between the first port 111 and the second port 112. A CNT array 100 according to the present invention may include millions of CNTs 110.

Figure 3:
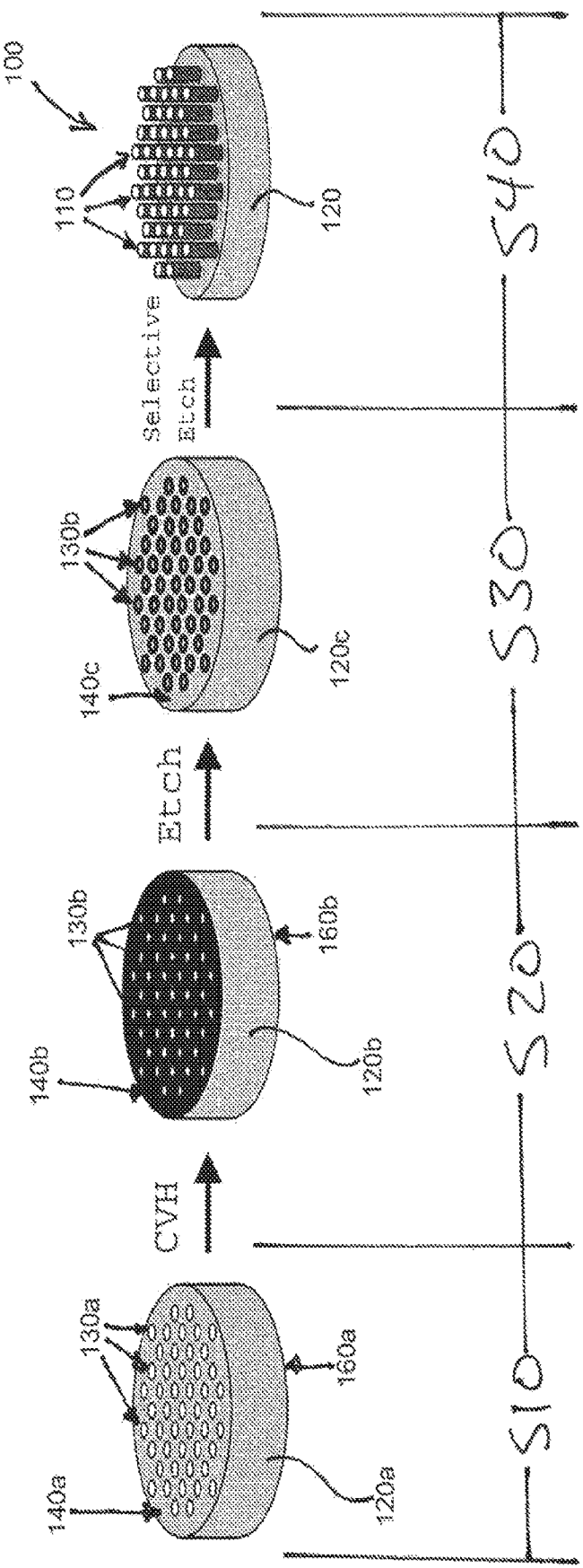
FIG. 3 shows a process for fabricating the CNT array shown in FIG. 1.

A CNT array 100 may be constructed via a template-based chemical vapor deposition (CVD) process, as schematically illustrated in FIG. 3. In a CVD process, carbon is deposited on the surface of a template by thermally decomposing a carbon carrying gas (for example: ethylene, methane or acetylene). Such a construction process includes, generally, subjecting a porous template substrate 120a, having a top surface 140a, a bottom surface 160a and a network of pores 130a, to a carbon CVD process so as to produce a carbon-coated substrate 120b having a carbon-coated top surface 140b and carbon-coated bottom surface 160b connected by a network of carbon-lined pores 130b. The carbon-coated substrate 120b is then etched to remove at least the carbon coating on top surface 140b of deposited carbon, and produce a carbon-lined substrate 120c having a top surface 140c of exposed template substrate material and the network of carbon-lined pores 130b connected to the carbon-coated bottom surface 160b. The carbon-lined substrate 120c is then selectively etched to remove a quantity of the exposed template substrate material to the exclusion of the carbon deposited in the carbon-lined pores 130b, thereby exposing the carbon-linings in the form of CNTs 110 protruding from a substrate base 120 formed of the template substrate material. Thus, in one aspect, disclosed herein are methods of making a carbon nanotube (CNT) array comprising a) depositing carbon on a porous anodized aluminum oxide (AAO) membrane by chemical vapor deposition; b) wherein the deposited carbon coats an entire surface of the AAO membrane, including internal surfaces of pores in the AAO membrane; removing deposited carbon on one side of the AAO membrane by etching (for example, oxygen plasma etching); and c) exposing an array of hollow carbon nanotubes by selectively etching the AAO membrane on the same side that deposited carbon was removed in step (b). A further detailed discussion of methods for constructing a CNT array 100 follows.

In a step S10, a template substrate 120a is selected for fabricating a CNT array 100, with consideration of the desired characteristics of the intended CNT array 100. For example, as the individual CNTs 110 in the CNT array 100 can be fabricated as carbon-linings in pores 130a of the template substrate 120a, consideration is thus given to the average inner diameter of the pores 130a and the average spacing between the pores 130a of the template substrate 120a as these parameters will dictate the average outer diameter $D_o$ of the CNTs 110 as well as the average spacing $L_c$ between CNTs 110 in the resultant CNT array 100 (see FIG. 2).

In one aspect of the present invention, a commercially available anodized aluminum oxide (AAO) membrane is selected as a template substrate 120a. It is understood and herein contemplated that the membrane used as a template substrate 120a can be any other heat resistant material that consists of similar pore structure, including, but not limited to glass or silicon. The template substrate 120a is first annealed between two quartz plates for 4 hrs to 6 hrs at the temperature chosen for CVD and allowed to cool to room temperature, to stabilize the planar structure of the template substrate 120a.

The AAO membrane 120a is selected with a network of pores 130a that have an average pore diameter (corresponding with the resultant average CNT outer diameter $D_o$ shown in FIG. 2) from about 50 nm to about 300 nm; preferably from about 100 nm to about 300 nm; more preferably from about 150 nm to about 275 nm; and most preferably from about 160 nm to about 250 nm. For example, the outer diameter $D_O$ can be at least about 50, 55, 60, 65, 70, 75, 80, 85, 90, 95, 100, 105, 110, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 152, 153, 154, 155, 156, 157, 158, 159, 160, 161, 162, 163, 164, 165, 166, 167, 168, 169, 170, 171, 172, 173, 174, 175, 176, 177, 178, 179, 180, 185, 190, 195, 200, 205, 210, 215, 220, 225, 230, 235, 240, 245, 246, 247, 248, 249, 250, 255, 260, 265, 270, 275, 280, 285, 290, 295, or 300 nm. The network of pores 130a in the selected template substrate 120a also has an average pore spacing (corresponding with the average spacing $L_c$ between CNTs 110, as measured from pore-center to pore-center, as shown in FIG. 2) from about 100 nm to about 600 nm; preferably from about 250 nm to about 500 nm; and more preferably from about 350 nm to about 450 nm. The AAO membrane may be one having either an ordered or randomized network of pores, provided that the network of pores is characterized by the forgoing average pore diameter and average pore spacing parameters.

In step S20, the template substrate 120a is subjected to a carbon CVD process, using carbon carrying gases such as ethylene, methane or acetylene, to deposit carbon on the template substrate 120a and within the pores 130a thereof, thereby forming a carbon-coated substrate 120b having a carbon-coated top surface 140b, a carbon-coated bottom surface, and a network of carbon-lined pores 130b. The carbon CVD process can be performed in a manner to deposit a sufficient quantity of carbon within the pores 130a to form continuous carbon-linings through the pores 130a, without fully closing the pores 130a (as shown in FIG. 2). In this way, the carbon-linings within the carbon-lined pores 130b present fully formed CNTs 110 extend through the network of pores 130a.

The average thickness of the carbon-linings (i.e., the average wall thickness $T_c$ of the CNTs 110, as shown in FIG. 2), as well as the average inner diameter of the carbon-linings (i.e., average diameter $D_i$ of CNT passage channel 113, as shown in FIG. 2) may be selected by controlling the CVD duration, temperature, and gas flow rate. In one aspect of the present invention, the template substrate 120a is subjected to a carbon CVD process for a duration from about 0.25 hrs to about 24 hrs (for example, 4, 5, or 6 hrs), at a temperature from about 600° C. to about 1200° C. (for example 650, 655, 660, 665, 670, 675, 680, 685, 690, 700, 705, 710, 715, 720, 725, 730, 735, 740, 745, 750, 760, 780, 790, 800, 820, 840, 860, 880, 900, 920, 940, 960, 980, 1000, 1020, 1040, 1060, 1080, 1100, 1120, 1140, 1160, 1180, or 1200° C.), with a gas flow rate from about 10 sccm to about 500 sccm (for example, 55, 56, 57, 58, 59, 60, 61, 62, 63, 64, 65, 66, 67, 68, 69, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 sccm). The CVD duration may preferably range from 2.5 hrs to about 10 hrs; and more preferably may be from about 4 hrs to about 6 hrs. The CVD temperature may preferably range from 625° C. to about 950° C.; and more preferably may be from about 675° C. to about 750° C. The CVD gas flow rate may preferably range from 20 sccm to about 300 sccm; and more preferably may be from about 50 sccm to about 70 sccm. By performing CVD under these conditions a wall thickness of 28+/−5 nm can be achieved at 700° C., 60 sccm and 5 hrs. The carbon film deposited on the template by CVD can be further annealed at higher temperatures (i.e., 1200° C. to 2400° C.) to form more graphitic CNTs in order to change their electrical and mechanical properties.

The carbon CVD process is controlled to yield an average carbon-lining thickness (i.e., a CNT wall thickness $T_c$) from about 5 nm to about 100 nm; preferably from about 15 nm to about 50 nm; and more preferably from about 23 nm to about 33 nm. For example, the CNT wall thickness can be about 5, 10, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, or 100 nm. The carbon CVD process is controlled to yield an average carbon-lining inner diameter (i.e., an average CNT passage channel diameter D) from about 10 nm to about 300 nm; preferably from about 50 nm to about 250 nm; more preferably from about 95 nm to about 205 nm; and most preferably from about 140 nm to about 160 nm. For example, the inner diameter can be at least about 10, 20, 30, 40, 50, 60, 70, 75, 80, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 155, 160, 165, 170, 171, 172, 173, 174, 175, 180, 181, 182, 183, 184, 185, 190, 195, 200, 205, 210, 211, 212, 213, 214, 215, 216, 217, 218, 219, 220, 221, 222, 223, 224, 225, 226, 227, 228, 229, 230, 235, 240, 245, 250, 255, 260, 265, 267, 268, 269, 270, 271, 272, 273, 274, 275, 276, 277, 278, 279, 280, 285, 290, or 300 nm As a result, the carbon layer 140b on top of the substrate 120b and the carbon layer 160b on bottom of the substrate 120b will have a thickness from about 10 nm to about 150 nm; preferably from about 10 nm to about 125 nm; and more preferably from about 10 nm to about 100 nm.

In step S30, the carbon-coated substrate 120b is etched to remove the carbon-coated top surface 140b so as to yield a carbon-lined substrate 120c having a top surface 140c of exposed template substrate material and the network of carbon-lined pores 130b and a carbon-coated bottom surface 160b. Preferably, the carbon-coated substrate 120b is etched to a sufficient depth that the openings to the carbon-lined pores 130b are substantially free of any flow-restricting carbon deposits, such that an average diameter of the openings to the carbon-lined pores 130b corresponds with the average inner diameter of the carbon-lined pores 130b (i.e., the passage channel diameter $D_i$). In this way, the resultant CNTs 110 will be provided with second ports 112 that have a flow profile that is uniform with the flow profile of the passage channels 113. Etching of the carbon-coated substrate 120b may be performed by oxygen plasma etching. In one aspect of the present invention, the carbon-coated substrate 120b is subjected to an oxygen plasma etching process for a duration from about 30 seconds to about 8 minutes, at an RF power from about 50 W to about 450 W, chamber vacuum from about 50 mTorr to about 400 mTorr, electrode spacing from about 0.75 cm to about 1.5 cm, and oxygen gas flow rate from about 1 sccm to about 100 sccm. The oxygen plasma duration may preferably range from 1 minute to about 5 minutes; and more preferably may be from about 2 minutes to about 4 minutes. The RF power may preferably range from 150 W to about 400 W; and more preferably may be from about 200 W to about 300 W. The oxygen plasma chamber vacuum may preferably range from 100 mTorr to about 400 mTorr; and more preferably may be from about 250 mTorr to about 350 mTorr. The oxygen plasma electrode spacing may preferably range from 1 cm to about 1.5 cm; and more preferably may be from about 1 cm to about 1.25 cm. The oxygen gas flow rate may preferably range from 50 sccm to about 100 sccm; and more preferably may be from about 80 sccm to about 100 sccm. Using these settings, the carbon layer 140*b* will be etched from 120b and expose substrate 140*c*. The carbon layer can also be etched by ion milling, or high temp oxidation preferably at 520° C.

In step S40, the carbon-lined substrate 120*c* is selectively etched at the top surface 140*c* to remove a quantity of template substrate material to the exclusion of the carbon deposited in the carbon-lined pores 130*b*. Such selective removal of the template substrate material exposed the carbon-linings in the carbon-lined pores 130*b* in the form of CNTs 110 that protrude from a substrate base 120 formed of a remaining quantity of the template substrate material. In one example, such as when an AAO membrane is selected as the template substrate 120*a*, selective etching of the template substrate material may be performed by reactive ion etching (RIE) using boron trichloride ($BCl_3$) and/or chlorine ($Cl_2$) gases. For example $BCl_3/Cl_2$ mixtures of 100%/0%, 75%/25%, 50%/50%, 257%/75% and 0%/100% of $BCl_3$ and $Cl_2$, respectively). Preferably the RIE is by boron trichloride ($BCl_3$) RIE alone. Thus, in one aspect, disclosed herein are methods of making CNT arrays wherein the carbon nanotube array is exposed by ME, for example, ME using boron trichloride ($BCl_3$)

The AAO membranes can also be selectively etched by wet chemical etching using sodium hydroxide (NaOH), phosphoric acid ($H_3PO_4$), sulfuric acid ($H_2SO_4$), hydrochloric acid (HCl), acetic acid ($CH_3COOH$), formic acid (HCOOH), or potassium hydroxide (KOH), and a combination of phosphoric acid and chromic acid. If other template materials are utilized (i.e., glass, silicon, or other high temperature-resistant materials), different selective etching techniques are to be used (e.g., Hydrofluoric acid wet-etches glass but not carbon). While wet etching can be used, wet etching with acids or bases can result in uneven and disordered exposed nanotube structures that did not transfer molecules efficiently into cells, so RIE is preferred.

The average height $H_c$ of CNTs 110 in the CNT array 100 (as shown in FIG. 2), as measured from the second planar surface 122 of the substrate base 120, may be selected by controlling the RIE duration, radiofrequency (RF) power, plasma chamber vacuum, electrode spacing and gas flow rate. In one aspect of the present invention, the carbon-lined substrate 120*c* is subjected to an ME process for a duration from about 2 hrs to about 5 hrs, at an RF power from about 50 W to about 400 W, chamber vacuum from about 10 mTorr to about 300 mTorr, electrode spacing from about 1 cm to about 4 cm, and $BCl_3$ gas flow rate from about 1 sccm to about 100 sccm. The ME duration may preferably range from 2.5 hrs to about 4.5 hrs (i.e., from about 150 min to about 270 min); and more preferably may be from about 3 hrs to about 4 hrs. For example the REI duration can be about 180, 190, 200, 210, 220, 230, or 240 min. The ME RF power may preferably range from 150 W to about 400 W (for example, 150 W, 175 W, 200 W, 225 W, 250 W, 275 W, 300 W, 325 W, 350 W, 375 W, or 400 W or any wattage in between); and more preferably may be from about 250 W to about 400 W. The RIE chamber vacuum may preferably range from 10 mTorr to about 200 mTorr; and more preferably may be from about 10 mTorr to about 300 mTorr. The ME electrode spacing may preferably range from 2 cm to about 3.5 cm; and more preferably may be from about 2.5 cm to about 3 cm. The RIE $BCl_3$ gas flow rate may preferably range from 50 sccm to about 100 sccm; and more preferably may be from about 80 sccm to about 100 sccm. Preferably, the carbon-lined substrate 120*c* is selectively etched to a sufficient depth that the average height $H_c$ of CNTs 110 in the resultant CNT array 100 (as measured from the top surface of the substrate base) is from about 100 nm to about 550 nm; preferably from about 150 nm to about 500 nm; and more preferably from about 170 nm to about 450 nm. For example the height of the CNTs 110 can be less than or equal to about 550, 549, 548, 547, 546, 545, 544, 543, 542, 541, 540, 535, 530, 525, 520, 515, 510, 505, 500, 495, 490, 485, 480, 475, 470, 465, 460, 455, 450, 445, 440, 435, 430, 425, 420, 415, 410, 405, 400, 395, 390, 385, 380, 375, 370, 365, 360, 355, 350, 349, 348, 347, 346, 345, 340, 335, 330, 325, 320, 315, 310, 305, 300, 290, 280, 270, 260, 250, 240, 230, 220, 210, 205, 200, 195, 190, 185, 180, 179, 178, 177, 176, 175, 170, 165, 160, 155, 150, 145, 144, 143, 142, 141, 140, 135, 130, 125, 120, 115, 110, 105, or 100 nm.

Immortalized cells (HEK293, L6) have not required pre-coating for adhesion to the CNT device. Human embryonic stem cells can be grown without feeder cells, allowing direct access to the stem cell membrane by our carbon nanotubes. Cells such as stem cells and primary T-cells often require a surface coating to adhere to a substrate. In one aspect, the CNTs 110 in the CNT array 100 (as shown in FIG. 2) can be coated with a substrate to promote adhesion of cells. It is understood that the substrate can be any known substrate known in the art for this purpose including, but not limited to, extracellular matrix (ECM) containing hydrogels (such as, for example, MATRIGEL® and CULTREX® BME), ECM components (such as, for example, laminin, fibronectin, poly-L-lisine and combinations thereof), and recombinant laminins such as Recombinant Human Laminin-521. Different coatings were tested to determine if the coatings enhanced cell adherence, and the results were scored according to morphology, viability and gene transfer. The CNT device was coated with substrates known to promote adhesion of stem cells, including MATRIGEL® (Corning, Inc.) which acts as an artificial basement membrane, a combination of poly-L-lysine (PLL) and laminin (LN), and a combination of fibronectin (FN) and laminin (LN), and recombinant human laminin-521. H7 embryonic stem cells (ESC) adhered best when plated on MATRIGEL® or recombinant laminin-521, and neuronal stem cells adhered well on CNT coated with MATRIGEL®. Cells were plated on the coated devices and grown for 48 hrs, and then stained on the device with calcein-AM (live cells) and Hoechst dye (nuclei) and imaged with fluorescence microscopy. To ensure that the coating material did not clog the nanotubes, the carbon nanotubes after coating were imaged by scanning electron microscopy (SEM) and no blocked CNTs were observed. MATRIGEL® did not block DNA transfer into stem cells. It is understood and herein contemplated that the use of a coating can increase cell adhesion to the CNTs 110 and the preferred coating can vary with the cell type that is adhering. For example, H7 embryonic stem cells adhered best when plated on MATRIGEL® or Recombinant Human Laminin-521 whereas Neural Stem cells adhered best to CNTs 110 that were coated with MATRIGEL® and primary neurons adhered best to Laminin coated CNTs 110.

FIG. 4 shows one example of a transfer system 300 according to the present invention. The transfer system 300 includes a CNT array 100 mounted to an administration platform 200. FIGS. 5a-5c shows examples of the administration platform 200. The administration platform 200 includes a base wall 210 and a sidewall 220 extending from a first side of the base wall 210. The sidewall 220 presents an opening 230 at an end opposite the base wall 210, the opening 230 being dimensioned for reception of a substrate base 120 of a CNT array 100.

Once mounted to the opening 230, the CNT array 100 may optionally be sealingly engaged to the administration platform 200 by application of a sealing material 310 or by suitable mechanical means. Suitable sealing materials may include, though or not limited to: Vacuum grease, petroleum jelly layer, wax, rubber O-ring. In one aspect, it is contemplated that the mechanical means for sealingly engaging the CNT array to the administration platform will cause a compressive force to be effected on the adjoined surfaces of the CNT array and administration platform. Examples of mechanical means of sealingly engaging the CNT array to the administration platform include, in this aspect, a male compression fitting, which can be configured to sealingly engage a female fitting to form a compression fitting. In one aspect, the female fitting can have a raised portion and the male compression fitting an indentation that when aligned form a lock. In an alternative example, the exterior perimeter surface of the CNT array 100 can comprise a raised perimeter with a convex bevel located at the mid-point to three-fourths point on the interior wall of the raised perimeter of the sidewall 220. The top surface of the administration platform 200 can have a perimeter relief that is of a depth to receive the male fitting on the CNT array 100. Additionally, the relief on the administration platform 200 can have a concave indentation, which can form a lock when the convex bevel of the CNT array 100 is engaged. Similarly, the CNT array 100 and administration platform 200 can be threaded in such a manner to allow the CNT array to be screwed down on the administration platform. Suitable sealing materials may include, though are not limited to: Vacuum grease, petroleum jelly layer, wax, rubber O-ring.

The base wall 210 and sidewall 220 define a well 240 for reception and containment of a volume of agents, such as nucleic acids or other foreign materials intended for transfer into target cells plated on a CNT array 100 mounted in the opening 230. In some examples, access to the well 240 is limited to only the opening 230. In other examples, as shown in FIGS. 5a-5c, the administration platform 200 may include an injection port 250 at the side wall 220 and/or base wall 210 that serves as an additional access means to the well 240. An injection port 250 may include a liquid tight, self-resealing barrier 251, as depicted in FIG. 4, such that a syringe needle may pierce the barrier 251 and, upon withdrawal of the syringe needle, the barrier 251 may reseal and continue to serve as a liquid tight surface of the well 240.

Optionally, the administration platform 200 may include one or more substrate support surfaces 260 that are positioned and dimensioned to abut the substrate base 120 and prevent the CNT array 100 from contacting the closed base wall 210. In some examples, as shown in FIG. 5a and FIG. 5b, one or more a support surfaces 260 may be provided at the side wall 220 in the form of a continuous or discontinuous annular ridge that protrudes into the inner volume of the administration platform 200. In other variations, the sidewall 220 may include a number of horizontal projections that protrude into the inner volume of the administration platform 200 and serve as support surfaces. In other examples, as shown in FIG. 5c, the base wall 210 may include one or more support surfaces 260 in the form of one or more protrusions (e.g., a plurality of vertical columns; a single continuous circular ridge; etc.) that protrude into the inner volume of the administration platform 200. In other variations, the administration platform 200 may be dimensioned to support the CNT array 100 on top of the array at the opening 230.

Figure 6:
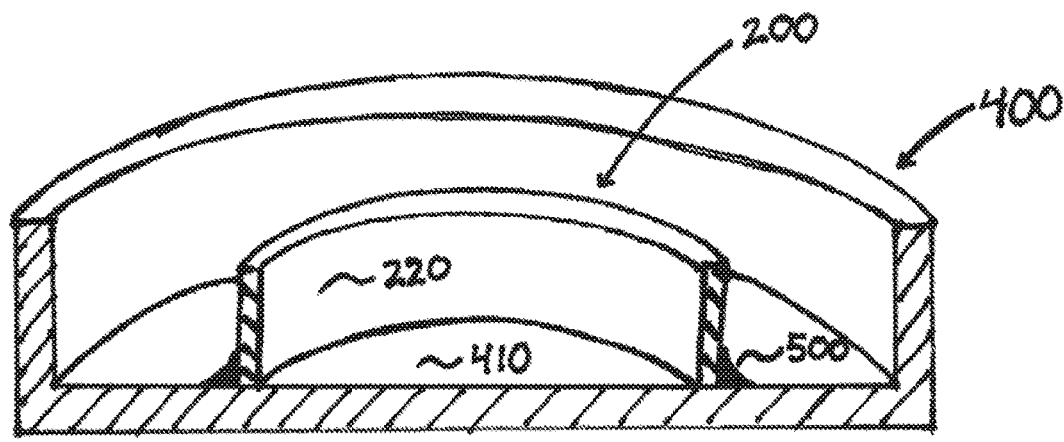
FIG. 6 shows a fourth example of an administration platform for use in the CNT transfer system shown in FIG. 4.

In some variations, the administration platform 200 may be constructed without a base wall, such that the administration platform 200 is characterized by a sidewall 220 having two open ends. In such examples, a well 240 may be formed within the perimeter of the side wall 220 by placing the administration platform 200 on a separate planar surface and introducing a water tight sealing material between the side wall 220 and the planar surface. For example, as shown in FIG. 6, the administration platform 200 may be placed in a tissue culture plate 400 and a quantity of watertight sealing material 500 may be applied along a boundary of the sidewall 220 and a planar surface 410 of the tissue culture plate 400. Suitable sealing materials may include, though or not limited to: Vacuum grease, epoxy, petroleum jelly layer, wax, and/or rubber O-ring. In variations omitting a base wall, any injection ports 250 and/or support surfaces 260 included in the administration platform 200 will be positioned at the side wall 220, with any included support surfaces 260 preventing the CNT array 100 from coming into contact with the planar surface (e.g., the planar surface 410 of the tissue culture plate 400).

In one aspect, the methodology can employ the use of a wicking substrate in the bottom of the dish soaked in media. An CNT array 100 can be placed so that cells are in contact with the wicking reservoir, and injection solution applied to the backside 160b. This administration method enables the injection to variable shaped devices (square, circular, triangular, etc.) or multiple devices simultaneously. Additionally, it is understood and herein contemplated that the CNT arrays can be used upright or inverted.

Figure 7:
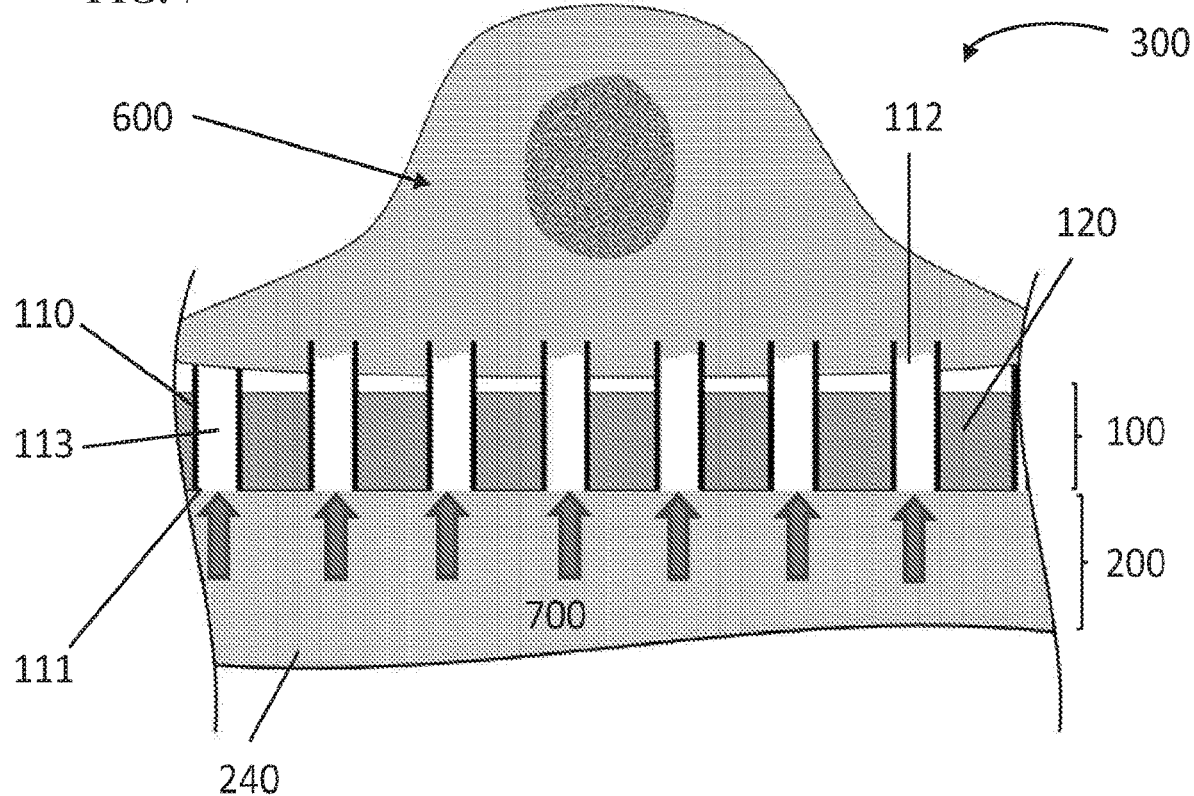
FIG. 7 is a schematic representation of an intracellular injection process performed with the CNT array shown in FIG. 1.

In preparing a transfer system 300 for use, as depicted in FIG. 7, target eukaryotic cells 600 are plated to a CNT array 100, and a quantity of agents 700 for injection into the target cells 600 is introduced into the well 240 of an administration platform 200. The CNT array 100 is then mounted to the opening 230 of the administration platform 200, as depicted in FIGS. 5a-5c. The target cells 600 may be any cell type desired for study via intracellular injection of a test agent, including though not limited to: immortalized cell lines such as human embryonic kidney 293 (HEK293); L6 myocyte cells; macrophage cells; primary cells (such as neurons); embryonic stem cells; and neuronal stem cells. The quantity of agents 700 may be any desired agent for injection into a population of target cells, including though not limited to: dyes; nanostructures (particles, rods, tubes); vesicles; micelles; RNA; DNA; peptides; proteins; carbohydrates; and small molecules.

If the administration platform 200 includes one or more support surfaces 260, such as those depicted in FIGS. 5a-5c, then the CNT array 100 is mounted in the opening 230 such that the substrate base 120 is supported on the one or more support surfaces 260. If the administration platform 200 lacks any support surfaces 260, then the CNT array 100 is mounted to the administration platform 200 such that the substrate base 120 is rests against the quantity of agents 700 contained in the well 240.

Mounting the CNT array 100 to the administration platform 200 places the first ports 111 of the CNTs 110 in fluid communication with the quantity of agents 700 contained in the well 240; and the first ports 111 will serve as inlet ports for entry of agents 700 into the passage channels 113, and transfer of agents 700 through the passage channels 113. In examples where the administration platform 200 lacks any support surfaces 260, the weight of the CNT array 100 resting on the quantity of agents 700 may generate an additional pressure force that further promotes fluidic transfer of agents through the first ports 111 and passage channels 113. The second ports 112 of the CNTs 110 serve as outlet ports for injection of agents to target cells 600 supported on the CNT array 100. The transfer system 300 remains in this configuration while agents 700 are transferred into the target cells 600 for a predetermined duration of time, or until the desired quantity of agents 700 has been transferred to into the target cells 600.

It is understood and herein contemplated that the disclosed CNT arrays, transfer systems and kits can be used for administering an agent such as a macromolecule, nanoparticle, or nucleic acid to a cell. Accordingly, disclosed herein are methods of administering an agent 700 (including, but not limited to dyes; nanostructures (particles, rods, tubes); vesicles; micelles; RNA; DNA; peptides; proteins; carbohydrates; and small molecules) into a cell with a carbon nanotube (CNT) array, comprising contacting the cell with a CNT array according to any preceding embodiment disclosed herein; wherein the cell is placed in contact with the second planar surface 122 of the substrate base 120 of the CNT array 100; wherein the CNT array 100 supports the cell without compromising the cell health or cell morphology; and wherein the agent is administered to the first planar surface of the base in a manner allowing flow of the agent into the inlet ports (i.e., first ports 111), through the fluid passage channels 113, and out the outlet ports (i.e., second ports 112) of the CNT array 100 so as to come into contact with the cell supported on the CNT array.

In some examples, such as when the quantity of agents 700 includes biomolecular agents that are transferred into target eukaryotic cells 600 via a CNT array 100, the predetermined duration of time may be any duration of time between 1 minute and 24 hours over a 24 hour period. For example, the duration of time for the transfer of the agent can be 1, 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, or 24 hours. In one aspect, the duration of transfer of the agent to the cell is between about 30 minutes and 12 hours; preferably, between about 1 and six hours, more preferably about 4 hours or less; and more preferably about 2 hours or less.

As noted previously, prior methodologies and devices for nucleic acid delivery can be very toxic to a cell. The toxicity can be inherent to the delivery method (such as viral or plasmid vector toxicity) or due to inefficiencies in the uptake of the agent due to the methodology requiring higher dosing. Also, the prior methodologies and devices can physically damage the cells or result in fragile cells such as that which occurs with lipofection. Therefore, the prior methodologies and devices are limited to single applications of an agent such as, a nucleic acid. The present CNT array and methodologies described herein are able to deliver nucleic acid or any other agent to a cell in a gentle manner and have much higher efficiency of transfer. Because significantly reduces physical damage to the cell and higher efficiency of uptake, reduced dosing can be used and agents, such as nucleic acids can be transferred multiple times over a 24 hour period of time and multiple injections can be made during a single transfer. Thus, for example, in one aspect disclosed herein are transfer systems and methods of administering an agent, wherein the agent can be transferred to the cells 1, 2, 3, 4, 5, 6, 7, 8, 9, 10, 11, or 12 times in one 24 hour period. Once injection of the agents 700 into the target cells 600 is completed, the target cells 600 may optionally be removed from the CNT array 100 to permit additional injection (e.g., with different agents) or further post-injection processing (e.g., re-culturing of the cells).

In a transfer system 300 that includes an administration platform 200 with an injection port 250, as depicted in FIGS. 5a-5c, the CNT array 100 may be mounted to the administration platform 200 prior to introduction of the quantity of agents 700 to the well 240, and the quantity of agents 700 may be subsequently introduced to the well 240 via the injection port 250. In such a transfer system 300, the injection port 250 may also be used to replenish the quantity of agents 700 in the well 240 after an initial amount of the agents is injected into the target cells 600 and/or to continuously feed agents into the well 240 for continued injection via the CNT array 100. In one example, the injection port 250 may be fluidically connected with an outlet of an external test agent supply source that continuously feeds a flow of agents to the transfer system 300. In examples where an external test agent supply source is used, the continuous feed of a test agent supply flow to the transfer system 300 may be performed at a flow rate that pressurizes the quantity of agents 700 in the well 240, thereby generating a fluid pressure force that further promotes fluidic transfer of agents 700 through the first ports 111 and passage channels 113 of the CNTs 110. In some aspects, transfer of the agent through the first ports 111 and passage channels 113 of the CNTs 110 can be accomplished by other motive forces, such as, for example, electrical, concentration gradients, or magnetic forces, in addition to or alternatively to pressure. Thus, in one aspect, disclosed herein are methods of administering an agent 700 to a cell, wherein the flow of the agent into the inlet port is by one or more motive forces including but not limited to electrical, magnetic, pressure, and/or concentration gradient.

Though not being bound by theory, it is believed injection of the transfer material into the target cells 600 is effectuated by one of two mechanisms. In a first theory, the tips of the CNTs 110 penetrate the cell membranes such that agents 700 are injected directly into the cells 600 upon exiting the second ports 112. In a second theory, the tips of the CNTs 110 support the target cells 600 without penetration of the cell membranes, and agents are transferred through the cell membrane by endocytosis. Regardless of the mechanism by which agents 700 enter the cell bodies, it is considered the relatively high packing per unit area of the CNTs 110 (as characterized by the spacing Lc in FIG. 2) and the relatively short height of the CNTs 110 (as characterized by $H_c$ or the length of CNT 110 from template surface 122 in FIG. 2) provide the CNT array 100 with a minimally invasive support structure that does not compromise the integrity of the cell membrane, allows for normal cell growth and proliferation on the tips of the CNTs 110, and facilitates removal by trypsinization of the cells with intact cellular membranes for additional post-injection processing. It is also considered the relatively high packing per unit area and relatively short height of the CNTs 110, together with a natural affinity that cells have for the carbon material in the CNTs 110, acts to enhance fluidic transfer of agents into the target cells 600.

CNT Transfer Kits

Transfer systems 300 according to the present invention may be provided in the form of a kit, which may include one or more CNT arrays 100 and one or more administration platforms 200. For example, a single kit may include a corresponding number of administration platforms 200 and CNT arrays 100; or the kit may include a plurality of CNT arrays 100 for use with only a single administration platform 200.

A CNT transfer kit according to the present invention may also be provided with any number of consumable supplies for use in intracellular injection via the CNT transfer system 300. For example, the kit may include a buffer supply. Examples of suitable buffers include, though are not limited to: Phosphate-buffered saline (PBS), serum-free media, or a buffer compatible with cytoplasmic physiology (e.g., 1 mM MgCl2, 1 mM EGTA, 148 mM KCl, 5 mM HEPES, 2 mM Phosphocreatin, 5 mM ATP, 5 mM phosphocreatine, pH 7.2). In one aspect, the buffer can comprise an energy source such as, for example, ATP and/or phosphocreatine.

A CNT transfer kit according to the present invention may also be provided with printed instructions for performance of one or more intracellular injection processes, including though not limited to a process such as that set forth in the working example herein.

In one working example of the present invention, a commercially available WhatmanAnodiscanodized aluminum oxide (AAO) membrane was selected as a template substrate. The AAO membrane had a 13 mm diameter, with an average surface pore diameter of 205±42 nm and a pore spacing of 187±36 nm. The AAO membrane was annealed between two quartz plates for 4 hours at 730° C., and subsequently subjected to a carbon CVD process at 700° C. with 60 sccm of 30/70 (vol %/vol %) ethylene/helium gas mixture for 5 hours to yield a carbon-coated substrate with deposited carbon-linings in pores of the AAO membrane, thereby forming CNTs inside the pores.

After the carbon CVD process, a carbon layer was removed from the carbon-coated substrate by oxygen plasma etching at RF 250 W, 300 mTorr, with 100 sccm of oxygen gas flow and for 3.5 minutes. Removal of the carbon layer yielded an exposed AAO planar surface with carbon-lined pores. Selective etching was then performed to the AAO surface of the carbon-lined substrate by RIE using borontrichloride ($BCl_3$) gas at 100 sccm, 150 mTorr, and RF 400 W for 195 minutes. Selective etching of the AAO material, to the exclusion of the carbon deposited within the pores of the AAO material, yielded an array of CNTs embedded in and protruding from a substrate base formed of the AAO material.

The CNT array in this example included CNTs having an average tip diameter of 205±42 nm, an average wall thickness of 28±5 nm, and an average exposed height of 176±34 nm (as measured from the top planar surface of the substrate base).

Figure 8:
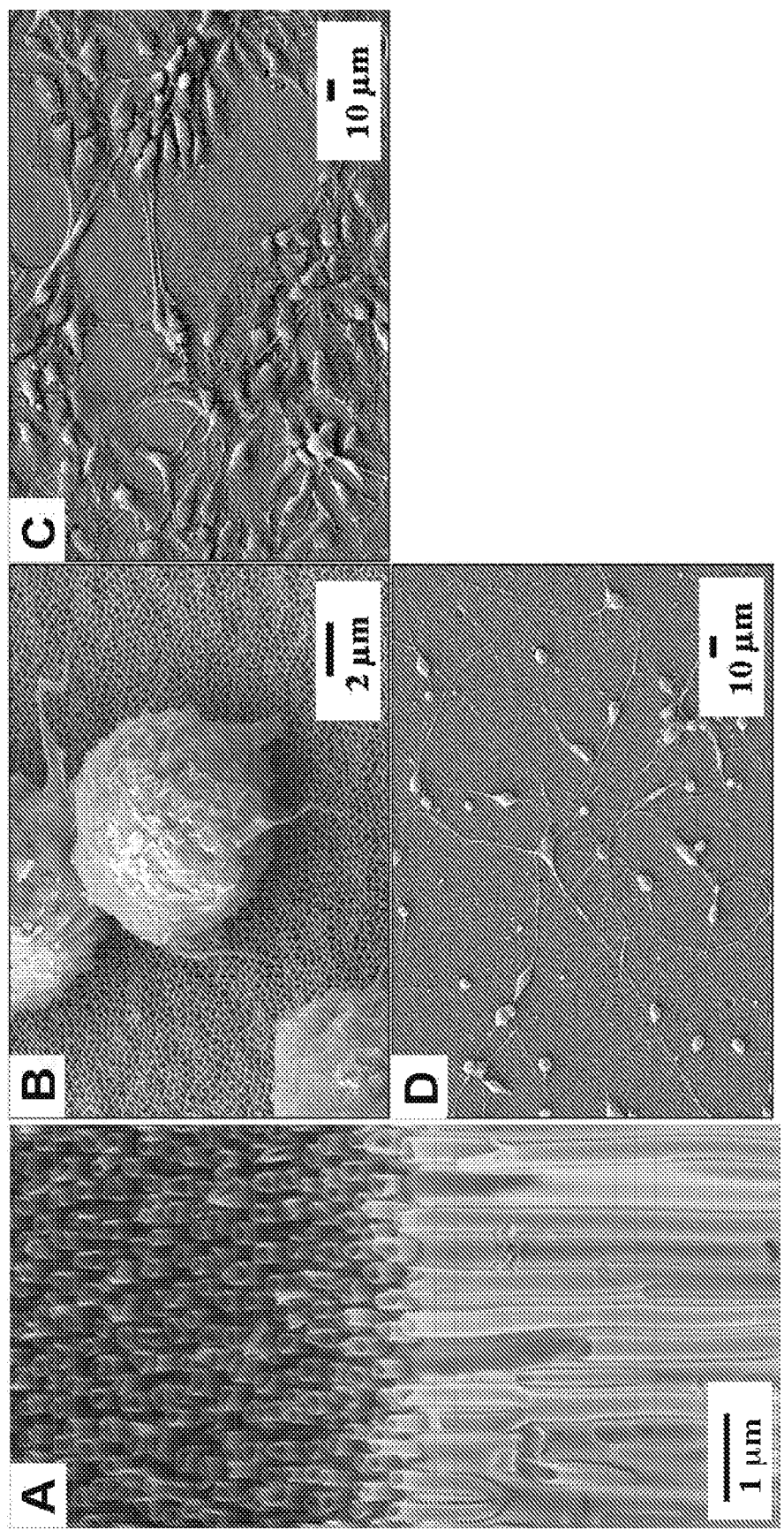
FIG. 8a shows a micrograph of the cross-section of the CNT array.
FIG. 8b shows mouse macrophage cells growing on top of CNT array.
FIG. 8c shows human neuronal stem cells growing on top of CNT array.
FIG. 8d shows human primary neurons growing on top of CNT array.
Figure 10:
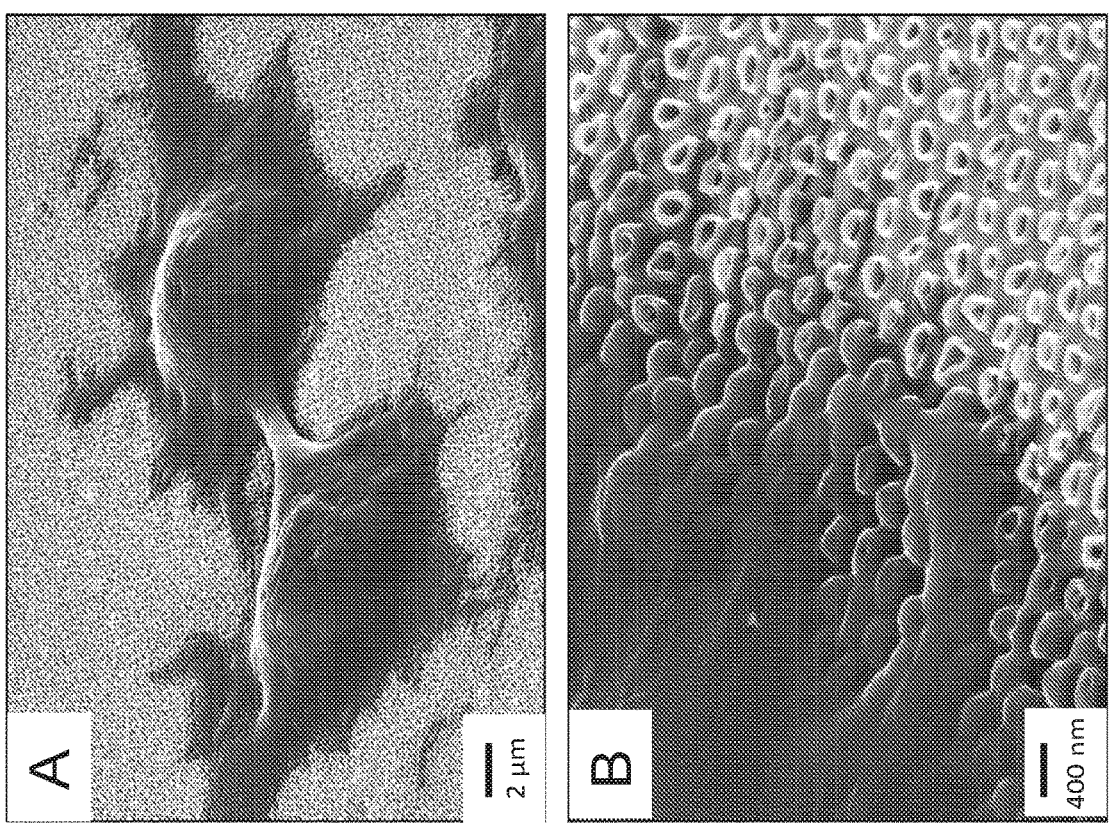
FIG. 10a shows micrograph of rat L6 myocyte cells growing on top of CNT array.
FIG. 10b shows higher magnification micrograph of basal side of rat L6 myocyte cells engulfing individual carbon nanotubes.

Such a conformation of relatively short, densely-packed CNT's facilitate cell growth by mammalian cells, including immortalized cell lines such as human embryonic kidney 293 cells (HEK293), RAW264.7 macrophage cells (FIG. 8b), human neuronal stem cells (FIG. 8c), human primary neurons (FIG. 8d) and L6 myocyte cells (FIG. 10a). Such short, closely packed CNT's encourage engulfment of CNT by basal cell membrane (FIG. 10b).

Cell viability on short, closely-packed CNT was validated by measuring cell proliferation and projected cell coverage area after seeding cells on CNT or on conventional plastic tissue culture plates. Cell growth on CNT devices was validated using HEK293 cells. The HEK293 cells, at approximately 40,000 cells/mL, were seeded in parallel on the CNT array and a similar-sized well of a conventional tissue culture plate, and both were monitored over 48 hours. The CNT devices and tissue culture plates were washed 3× with PBS to eliminate unattached and free floating cells and then were stained with live/dead assay, calcein-AM/ethidium homodimer-1, (Life technologies, L3224) before imaging. Cell spreading and proliferation were determined by fluorescence microscopy considering the live cells, and analyzing 20 sample images at two different magnifications (10× and 50×) and quantified using ImageJ software. Number of live cells stained by calcein-AM per surface area and the projected area of spread cells was extracted. The comparison was made by conducting a t-test between the cells cultured on tissue culture plate and CNT array at each time spot and using the p-values. FIG. 9a shows number of grown cells and FIG. 9b shows percentage of cell spreading, as observed at 3 hours, 24 hours, and 48 hours. The error bars in FIG. 9a and FIG. 9b indicate the standard deviation of 20 sampled images for each case. There was not observed any significant difference in cell coverage or number of cells between the CNT array and the conventionally loaded culture plates in the first three hours after seeding; and the target cells were observed to proliferate on the CNT arrays at the same rate as on conventionally loaded tissue culture plates. However, after 24 and 48 hours, the inventive CNT array was observed as promoting higher cell proliferation with comparable spreading compared to the conventionally loaded tissue culture plates. Cells cultured on top of the inventive CNT array for 48 hours were then trypsinized and re-cultured on a tissue culture plate for an additional 24 hours, and counted using a live/dead cell viability assay. There was determined a 97% cell viability, indicating that inventive CNT array can support cell culture comparable to conventional tissue culture plates.

Transfer of biomolecules into mammalian cells using the CNT array was demonstrated using HEK293 cells and rat L6 myocyte cells. As target cells, HEK293 and rat L6 myocyte were cultured in DMEM supplemented with 10% fetal bovine serum and 1% antibiotics at 37° C. and 5% $CO_2$, and 40,000 cells/mL were introduced on each CNT array and cultured for 48 hours before injection. On average, a single cell covered the protruding tips of approximately 900 CNTs; with the textured surface of tightly packed, short protruding CNT tips providing a support for cell adhesion.

Administration platforms having a tubular shape with a cylindrical sidewall dimensioned to accommodate a single 13 mm diameter AAO membrane, and without any base wall, were sealed to the planar surface of tissue culture plates to define culture wells between the cylindrical side walls of the administration platforms and respective planar surfaces of the tissue culture plates.

Figure 11:
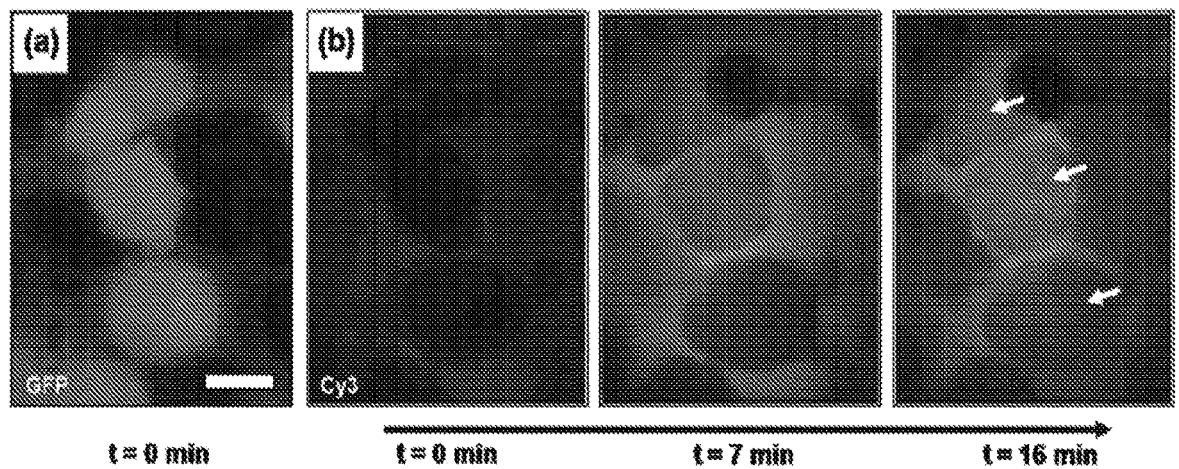
FIG. 11 shows the intracellular transfection of cells with membrane-impermeable dye using CNT array.
Figure 12:
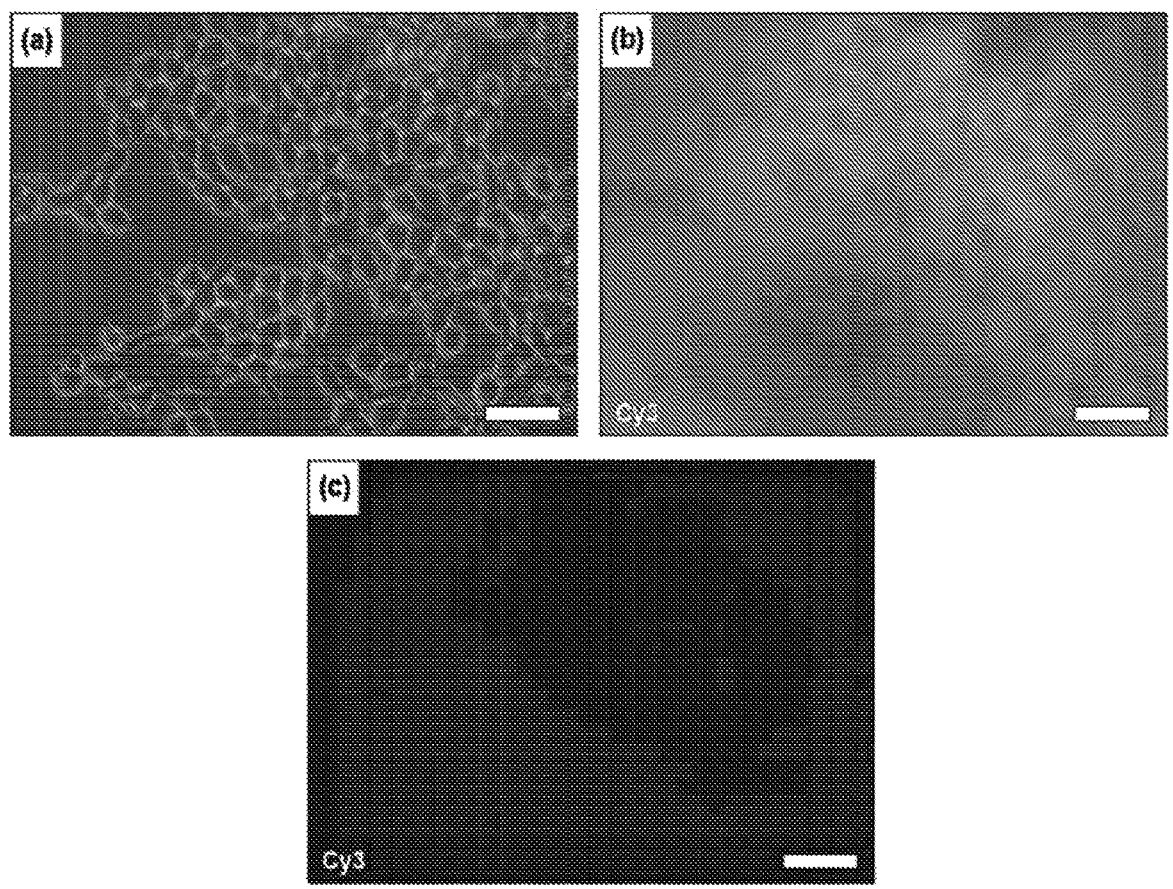
FIG. 12 shows permeation control of tetramethylrhodamine (dextran) into cells.
Figure 13:
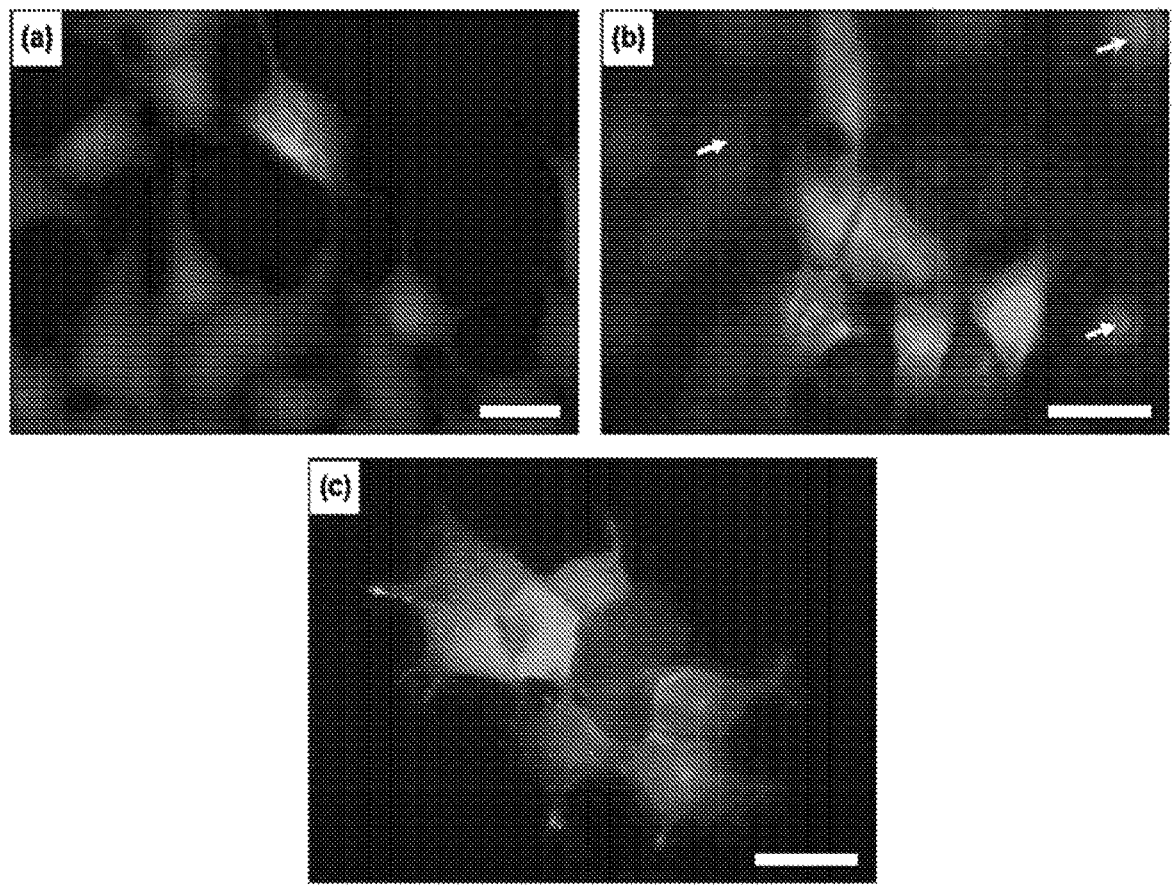
FIG. 13 shows intracellular transfection of cells with quantum dots by CNT array.

The CNT array device was utilized to deliver cell-impermeable molecules, such as macromolecules, nanoparticles, and nucleic acids into cells cultured directly on its surface. These molecules are unable to efficiently penetrate through the cell plasma membrane without a transport technique or reagent. Here, HEK293 cells were cultured on top of the CNT array for 48 hrs. The device was then removed from the culture media and positioned under an upright fluorescent microscope on a custom perfusion stage to prevent cell dehydration during transfection. To demonstrate delivery into cells through the device, a 10 µM droplet of tetramethylrhodamine (dextran) dye was placed under the device and allowed to diffuse through the CNTs and into HEK293 cells cultured on the top surface of the device and incubated in growth medium containing 10 µM dextran, the same dextran concentration utilized for transfection. The cells and delivery were observed in real time under a fluorescent microscope (FIG. 11A and FIG. 11B). As shown in FIG. 11B, dye delivery through the CNT array device occurred within 16 min and cells remained viable throughout the process. No intracellular dye was observed when control cells grown on tissue culture plastic were incubated with dye added to growth media (FIG. 13). Control experiments were conducted to ensure impermeability of dextran molecule. Cells were incubated for 20 minutes (the required time for intracellular delivery of biomolecules with the device) (FIG. 13b), then rinsed, trypsinized and re-cultured in tissue culture plate. Evaluation of the cells by fluorescence microscopy showed no fluorescence in cells (FIG. 13c), indicating membrane impermeability of dextran.

Cells cultured on the CNT array device can be transfected, removed from the device, and cultured in standard tissue culture plates. Using the transfection and cell culturing protocols described above, HEK293 cells were cultured on the CNT array device and green fluorescent quantum dots (Qdots, 15-20 nm diameter) were delivered into the cell cytosol. The cells were then trypsinized from the device to stop transfection, and re-cultured in a tissue culture plate for 5 hrs. Results show efficient transfer of fluorescent Qdots (FIG. 13). Cells remained viable before, during, and after both the delivery and re-culturing process, as determined using the live/dead assay.

Figure 14:
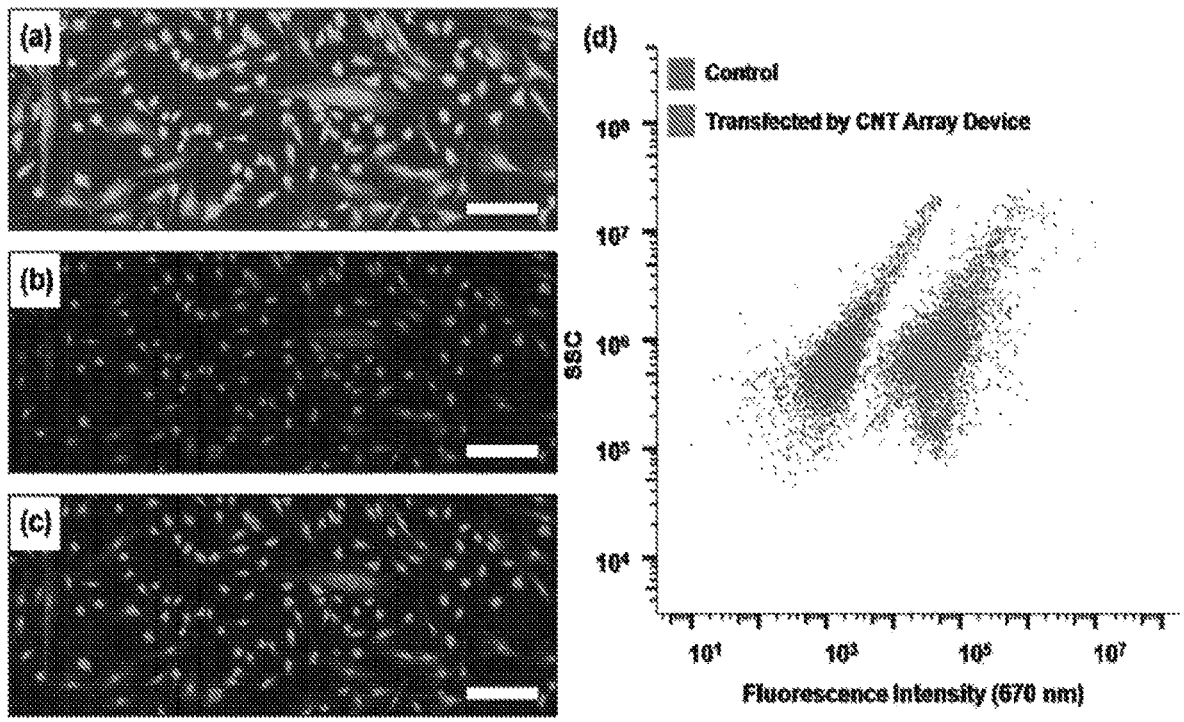
FIG. 14 shows high-efficiency dye transfer into cells using CNT array.

To facilitate large-scale transfection, a platform was developed consisting of a media-filled cylinder on which a CNT array, with cells cultured on its surface, was inverted and placed on top. Once in place, injection solution was applied to the backside of the inverted CNT array while keeping the cells bathed in growth media during the transfection. Using the custom platform, populations of cells were efficiently transfected with fluorescent dye. 40 000 L6 cells were seeded on the CNT array and cultured for 48 hrs. Cells were stained with calcein-AM dye to identify live cells (FIG. 14A). The device was then inverted and placed on the transfection platform to keep cells hydrated. A 50 µL drop of 75 µM propidium iodide (PI), a red membrane-impermeable dye, was placed on the backside of the device and allowed to diffuse through the CNTs and into the cells for 20 min. Cells were imaged (FIG. 14a, FIG. 14b, and FIG. 14c), and then trypsinized to stop transfection and collected for flow cytometry. Using fluorescence microscopy, almost all the cells appear to be both alive (stained green with calcein-AM) and transfected with dye (red fluorescence) (FIG. 15b). These results were confirmed by flow cytometry analysis, where 98% of the cells stained green (alive) and 99% of the viable cells were transfected with PI (FIG. 14d). These results demonstrate that the CNT array is able to transfect mammalian cells with high efficiency and minimal impact on cell viability within a short period of time.

Figure 15:
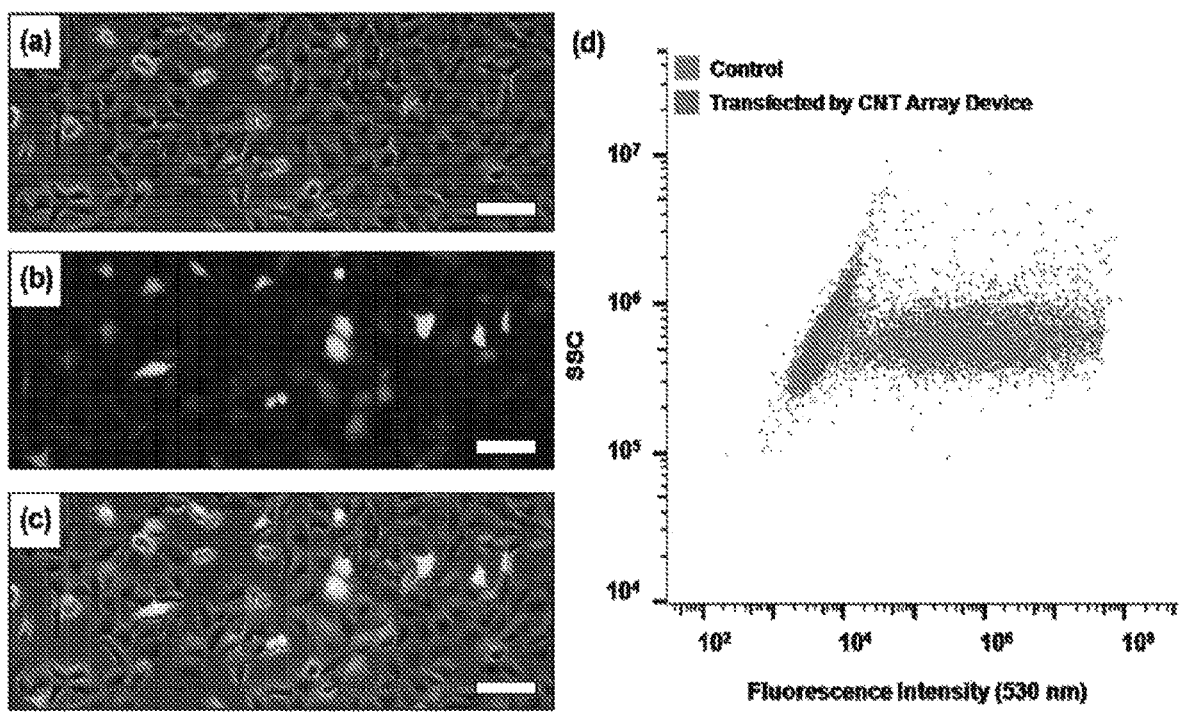
FIG. 15 shows high-efficiency plasmid transfection of cells using CNT array.
Figure 16:
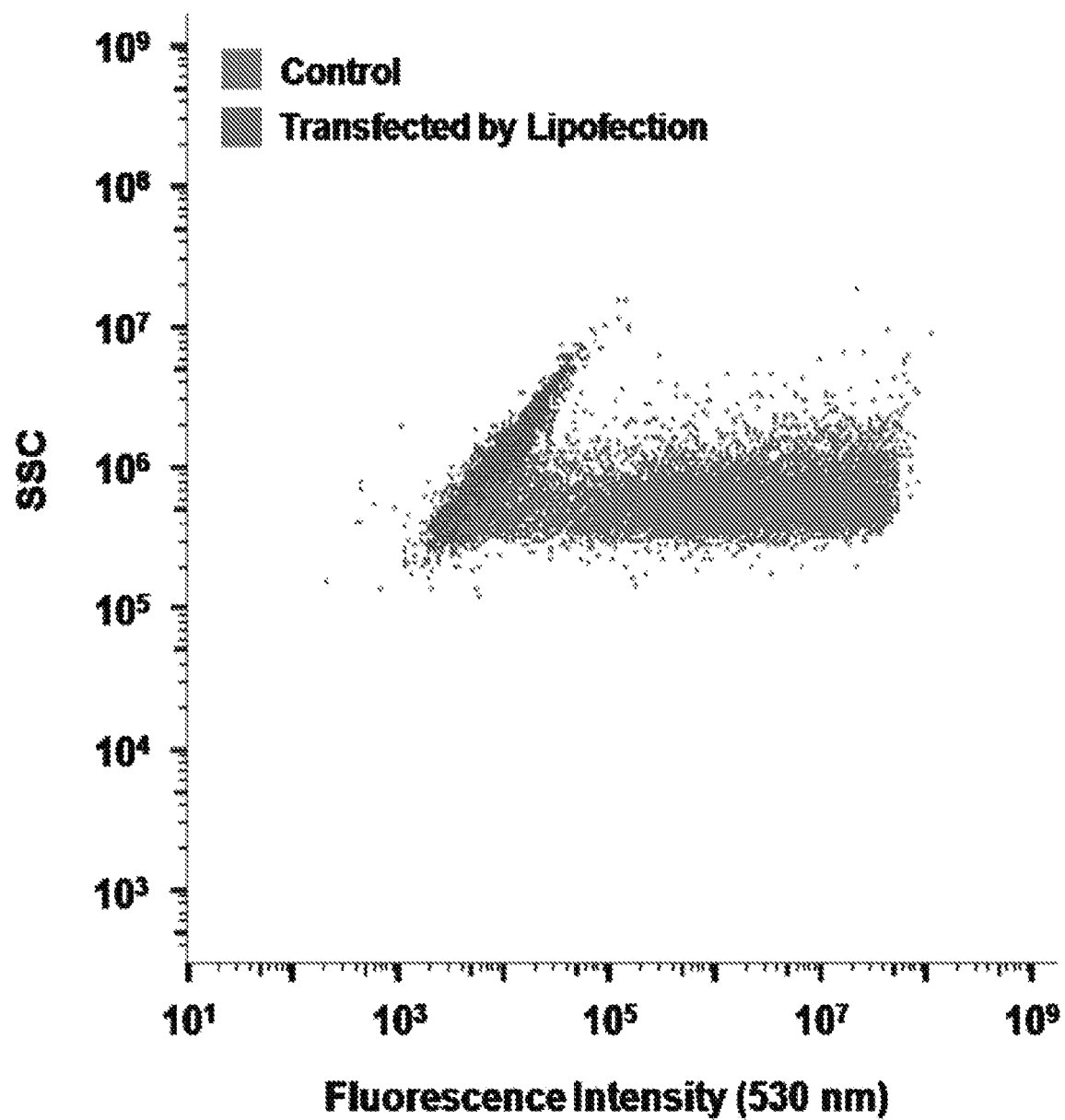
FIG. 16 shows flow cytometry results of HEK293 cells transfected with plasmid DNA encoding EYFP by lipofection. Transfection indicated by rightward shift in the 530 nm fluorescence intensity of injected cell population (red) compared to control uninjected (blue) cells. 30,000 cells were counted for each sample population.

The CNT array can efficiently transfer plasmid DNA into large populations of cells. 40 000 HEK293 cells were seeded on the device and cultured for 48 hrs. The device was inverted and placed in the custom transfection fixture containing growth media to keep cells hydrated. A 50 µL drop of 500 ng/µL plasmid DNA encoding enhanced yellow fluorescent protein (EYFP) was placed on the backside of the device and allowed to diffuse through the CNTs and into the cells for 2 hrs in a tissue culture incubator. Cells were then trypsinized to stop transfection, collected, transferred to tissue culture plate and cultured for 2 days. The EYFP expression in cultured cells was confirmed by fluorescence microscopy (FIG. 15a, FIG. 15b, and FIG. 15c). Due to variation of EYFP expression level, a gradation of fluorescence was observed, indicated as a continuum of low to high fluorescence intensity in the transfected population. The cells were then trypsinized and collected for flow cytometry. Quantification of transfection efficiency by flow cytometry showed that out of 25 000 counted cells, 84% of them were alive and expressing EYFP (FIG. 15d). These results demonstrate that the CNT array is able to transfer DNA into tens of thousands of cells with high efficiency and high cell viability. This device can achieve gene transfection efficiency comparable to well-established transfection methods, e.g., lipofection, but can do so within a shorter amount of time (FIG. 16).

The array of hollow CNTs described in the current studies is able to deliver macromolecules, nanoparticles, and DNA into tens of thousands of cells simultaneously with high efficiency and low toxicity. The CNT device provides the ability to accommodate a wide range of sizes of biomolecules, from 0.66 kDa (propidium iodide), 3 kDa (tetramethylrhodaminedextran) to 3900 kDa (6000 bp plasmid DNA). This wide range of cargo size indicates that the CNT array has broad use for transferring DNA, proteins, or drugs into cells. Results show highly efficient delivery of dye (99%) and plasmid DNA (84%) into tens of thousands of cells from two different cell lines, demonstrating the robustness of the hollow CNT arrays for efficient biomolecular delivery, with low toxicity. The CNT device is easily manufactured and utilizes standard cell culture consumables and procedures, making it amenable for broad application. By applying a sample solution to the backside of the CNT array and delivering the cargo molecules through the hollow CNT, the delivery concentration and cell-cargo contact time can be precisely controlled, and, serial delivery of multiple biomolecules is possible.

The enhanced capabilities of CNT-devices are used to transfer complex cargo into cells to develop model systemsUndesired (off-target) gene editing events can be significantly decreased by use of HDR. However, this approach requires the co-delivery of recombinant Cas9n (nickase) pre-packaged with targeting guide RNA (gRNA) and the HDR oligonucleotide, a very inefficient process in many desirable target cells, such as pluripotent stem cells (ESC and iPSC). However, as disclosed herein this approach has been adapted for use with CNT devices. Utilizing the optimal configuration of device and CRISPR components, a targeted mutation can be introduced into cells to recapitulate a disease and the resulting cells can be tested for the cellular effect of this mutation to develop a model system.

Additionally, the CNT arrays, kits, and methods disclosed herein work with cell types that are resistant to standard techniques with high translational applicability, such as human embryonic stem cells and iPSCs. Typically, high efficiency gene transfer into stem cells primarily done by viral infection, which has severe size limits on the genetic material that can be transferred, limiting use of current technologies such as CRISPR for gene editing, and cannot be used to transfer recombinant protein. Moreover, serial transfection of cells, such as for reprogramming of primary cells to generate iPSCs, is toxic to cells resulting in low efficiency and high screening costs for production of iPSCs. The low cytotoxicity and high transfection efficiency associated with CNT mediated gene transfer has great potential to increase efficiency of iPSC production. CNT-mediated gene transfer into primary human T-cells can aid development of CAR-T therapy, and into primary rodent T-cells speeds development of new models for disease.

Experiments have been carried out with GFP plasmid DNA at a concentration of 500 ng/µl for 2 hrs. The optimal concentration and exposure time for cargo (i) GFP plasmid DNA (ii) In vitro transcribed GFP mRNA (iii) recombinant GFP (Clontech) can be determined by flow cytometry following transfection. The effect of time on cargo delivery can be tested, exposing the cells to cargo for 0.5, 1, 2, 4 hrs, and cargo concentration, using 50, 100, 500, 1000 ng/µl of cargo for each of the incubation times above. All cargo is commercially available, including mRNA encoding EGFP that is 5' capped and 3' polyadenylated for expression in mammalian cells (TriLink Biotech) except for the plasmid DNA, which contains EGFP that were cloned into the expression plasmid pcDNA3.1 (Invitrogen). A 14 kb plasmid s constructed that encodes green fluorescent protein and transfection efficiency of this larger plasmid compared with the standard 6 kb plasmid. This is important for CRISPR gene editing, where four components need to be transfected (plasmids encoding Cas9n, two plasmids encoding gRNA, plus an oligonucleotide for homology-directed recombination), and for reprogramming primary cells to produce iPSCs, which require transfection of a mixture of 4-5 plasmids encoding transcription factors to induce pluripotency. Cells can be co-transfected with plasmids encoding three fluorescent markers that can be simultaneously detected and distinguished by flow cytometry: cyan fluorescent protein (CFP), yellow fluorescent protein (YFP), red fluorescent protein (RFP), and an HA-tagged β2-adrenergic receptor which can be detected with secondary antibodies linked with APCH7 fluorochrome (far red).

To test the utility of CNT for delivery of large and multicomponent genetic tools, CNTs can be used to enhance the efficiency of CRISPR/Cas9n-mediated gene editing. The rapid development of CRISPR/Cas9-mediated genome engineering has enabled unprecedented genetic manipulation of mammalian cells. However, genome engineering using homology-directed recombination (HDR) with the CRISPR/Cas9n system requires the delivery of multiple genetic elements into the target cell population. These components include: two guide-RNA (gRNA) expression plasmids, a plasmid expressing the Cas9n enzyme and single-stranded DNA template (HDR-template) that encodes the sequence that is to be inserted into the genome. The transduction of these multiple components using current transfection methods remains inefficient, resulting in laborious down-stream screening steps to arrive at a homogenous population of genetically targeted cells. Increasing the efficiency of transduction by using CNTs has the potential to over-come these problems.

CNT-mediated delivery of CRISPR components can be demonstrated in immortalized cells and H7 stem cells that are engineered to express GFP cDNA containing a point mutation that inactivates fluorescence (EGFP-Y107*). The gRNA and HDR can be designed to target a reversion point mutation in the inactive GFP, and screen for gain of fluorescence. H7 cells serve as a test for gene editing in stem cells and have been used for pilot CNT-mediated gene transfer experiments. Three configurations of CRISPR/Cas9 editing can be tested: a) All components encoded by DNA with plasmids encoding Cas9, gRNA, and co-delivery of the HDR oligonucleotide template b) All components (except HDR oligonucleotide template) encoded by in vitro transcribed RNA; and c) Recombinant Cas9 protein+in vitro transcribed gRNA+HDR oligonucleotide template. Conditions a) and b) can be compared to parallel experiments using lipofection to introduce the nucleic acids into cells to determine differences in nucleic acid transfer.

A DNA range of CRISPR/Cas9n vector (pSpCas9n(BB)-2A-Puro (PX462) V2.0, Addgene) of 150, 300, 600 and 1200 ng per CNT can be tested. Guide RNAs can be cloned into the pSpCas9n(BB)-2A-Puro and phH1-gRNA plasmids (Addgene).

H7 cells can be plated on CNT, grown for 48 hr, and transfected by CNT or lipofection. Harvested cells can be replated using standard conditions in tissue culture plastic, and cultured for 7 days. Gene editing to revert the inactivating point mutation in GFP can be monitored using a plate-based cell cytometer (Celigo, Nexcelom, Lawrence/MA). The reversion frequency, calculated as a percentage of cells that fluoresce green (reversion mutation), can be used to assess the effect of altered amounts of Cas9 and gRNA plasmid injected. Cells can be isolated for genomic sequencing to determine the rate of off-target mutations.

These studies identify the optimal conditions for CRISPR gene editing using our the CNT devices. These conditions can be used for DNA transfer as a guide for CRISPR editing using in vitro transcribed RNA instead of plasmid. RNA does not need to be transported to the nucleus and simplifies the intracellular trafficking requirements, is amenable for later use in post-mitotic cells such as primary neurons, and has been shown to increase the rate of targeted mutation in stem cells. Capped mRNA can be transcribed in vitro from the CRISPR plasmids described in the first half of the aim or subcloned into appropriate plasmids, and RNA can be transferred by CNT device as described above for plasmid DNA. Cells can be scored by fluorescence for rate of reversion mutation, and candidate cells can be harvested for genomic sequencing to determine the rate of gene editing, and the rate of targeted mutation versus off-target mutation.

The capabilities of CNT devices to transfer a cargo of mixed recombinant Cas9 protein (Thermo Fisher Scientific) preformed with gRNA targeting the GFP reversion mutation can also be exploited. Using recombinant Cas9 protein pre-complexed with gRNA can minimize off-target mutations that arise as a result of uncomplexed Cas9 in the target cell. Recombinant Cas9 has been used for CRISPR editing in cells, but it does not yet transfer with high efficiency by lipofection. This is an ideal use for the enhanced capabilities of carbon nanotube-mediated delivery.

Additionally, the CNT arrays, kits, and methods disclosed herein work with cell types that are resistant to standard techniques with high translational applicability, such as human embryonic stem cells and iPSCs. Typically, high efficiency gene transfer into stem cells and iPSCs is primarily done by viral infection, which has severe size limits on the genetic material that can be transferred, limiting use of current technologies such as CRISPR for gene editing, and cannot be used to transfer recombinant protein. Moreover, serial transfection of cells, such as for reprogramming of primary cells to generate iPSCs, is toxic to cells resulting in low efficiency and high screening costs for production of iPSCs. The low cytotoxicity and high transfection efficiency associated with CNT mediated gene transfer has great potential to increase efficiency of iPSC production. CNT-mediated gene transfer into primary human T-cells can aid development of CAR-T therapy, and into primary rodent T-cells speeds development of new models for disease.

Device Manufacturing:

CNT arrays were fabricated using commercially available anodized aluminum oxide (AAO) membranes (WhatmanAnodisc 13). CNTs were formed inside the AAO membrane using previously established processes. Briefly, AAO membranes were annealed in air at 730° C. for 4 hrs and placed in a three-stage CVD tube furnace (Carbolite TZF17/600). After purging the furnace with Argon, 30/70 (vol %/vol %) ethylene/helium precursor gas was flowed at 60 sccm into the furnace at 700° C. for 5 hrs to deposit a thin film of carbon on all surfaces of the AAO membrane, including the walls of the membrane pores to form CNTs embedded in the AAO template. The carbon layer on one side of the membrane was then removed using oxygen plasma (LAM 490) at 300 mTorr, RF 250 W, and oxygen flow rate of 100 sccm for 3.5 min. CNTs were then partially exposed by selectively etching the AAO template using reactive ion etching (LAM 4600) with boron trichloride ($BCl_3$) at 150 mTorr, RF 400 W, and $BCl_3$ flow rate of 100 sccm for 180 min. The resultant CNT array consisted of millions of CNTs (average tip diameter of 205±42 nm, tube wall thickness of 28±5 nm, tube-to-tube spacing of 187±36 nm) protruding 176±34 nm from the surface of the 13 mm diameter AAO membrane.

Dozens of CNT array devices were produced in a single manufacturing run and stored until needed for transfection.

Plasmid Preparation:

The pEYFP mammalian expression vector mVenus-C1 was maintained in *E. coli* DH5 a cells. Plasmid DNA was isolated from overnight *E. coli* cultures using commercially available kits (QIAGEN Plasmid Plus Midi Kit).

Cell Culturing:

Human embryonic kidney 293 cells (HEK293) and rat L6 myocyte were cultured in DMEM supplemented with 10% fetal bovine serum and 1% penicillin/streptomycin at 37° C. and 5% CO 2. 40 000 cells were counted by hemocytometry and introduced on each device and cultured for 48 h before transfection.

Cell Growth Study:

60 000 cells were plated on the device and on a control well in a 24-well tissue culture dish and stained with 5 μM calcein AM/ethidium homodimer-1 (Life technologies, L3224) in PBS before imaging. The CNT devices and tissue culture plates were washed 3× with PBS before imaging to eliminate unattached and free floating cells. Cell spreading and proliferation were determined by fluorescence microscopy, analyzing 20 sample images at two different magnifications (10× and 50×) and quantified using ImageJ software. The number of live cells stained by calcein AM per surface area and the projected area of spread cells was calculated (200-850 counts on average). For cell growth and spreading at each time step, statistical significance between the tissue culture plate and CNT array samples was determined by p-values obtained from t-tests.

Cell Transfection:

Transfection of cells was performed on a custom stage and controlled environment under the fluorescent microscope. Before transfection of the tetramethylrhodamine (dextran) and quantum dots (Qdots), HEK293 cells were counterstained with 2 μM calcein AM dye (Life Technologies, L3224) to be visible under the fluorescent microscope. A 10 μM solution of membrane-impermeable 3000 MW dextran in PBS (Life technologies, D3308) was prepared and introduced into the inlet of the transfection stage and the process was monitored by fluorescent imaging every 0.5 s.

Qdot transfection was conducted by preparing an 80 nM solution of carboxyl Qdots (Life Technologies, Q21341MP) in PBS. Delivery process was monitored by fluorescence microscopy (FIG. 13). Human embryonic kidney 293 (HEK293) cells were seeded on top of the device for 48 hours and stained with live assay (calcein AM), as shown in FIG. 13a. A solution of 80 nM carboxyl Qdots in PBS was prepared and introduced on the back side of the device over the custom stage for 20 minutes. The transfected HEK293 cells were then washed three times with PBS to remove suspended Qdots before imaging. Cells were then trypsinized and re-cultured on tissue culture plates for 5 hours, after which they were imaged again (FIG. 13c). As shown in FIGS. 13b and 13c, fluorescent Qdots are distinctly visible inside calcein-stained HEK293 cells after delivery (FIG. 13b), and 5 hours after transfection and re-culturing (FIG. 13c). Since the cells can uptake molecules from solution through endocytosis, control experiments were conducted to ensure impermeability of Qdots. To this end, cells were cultured on a standard tissue culture plate and incubated in growth medium containing 80 nM Qdots, the same Qdot concentration utilized for transfection. Cells were incubated for 20 minutes (the required time for intracellular delivery of biomolecules with the device), then rinsed, trypsinized and re-cultured in culture plate and evaluated by fluorescence microscopy. No intracellular Qdots were observed in these control cells, indicating membrane impermeability of Qdots.

Cells were also transfected with 75 μM solution of PI in PBS. For these studies L6 cells were cultured on the CNT array device for 48 h, after which they were stained with 2 μM calcein AM dye to identify the live cells as shown in FIG. 15. PI delivery was conducted in the custom stage, keeping the cells hydrated in PBS. After 20 min, cells were trypsinized and collected in 100 μL of complete serum-free medium (CSFM, DMEM supplemented with 2 mg/mLBSA, 25 mM HEPES pH 8.0, 1% penicillin/streptomycin, 1 ng/mL transferrin, 1.25 ng/mL insulin) for flow cytometry. Control experiments were conducted to ensure impermeability of PI at the concentrations in which the cells were transfected. To this end, 40,000 L6 cells were cultured on standard tissue culture plates for 48 hours. Cells were incubated in serum-free medium (CSFM, DMEM supplemented with 2 mg/ml BSA, 1% penicillin/streptomycin, 1 ng/ml transferrin, 1.25 ng/ml insulin) containing 10 μM PI (concentration represents the extreme scenario, where the entire 50 μL injection volume of 75 μM PI entered into the serum-free medium reservoir) for 20, 40, and 60 minutes. Cells were then trypsinized and collected for flow cytometry. For each incubation time, 30,000 cells were analyzed by flow cytometry. The results showed that the PI does not permeate into cells incubated up to 40 minutes (double the time used to inject cells through the CNT array), and PI permeated only 5% of the cells incubated for 60 minutes.

For transfection of plasmid DNA, HEK293 cells were seeded and cultured on the device as described above for 48 hrs. A 500 ng μL$^{-1}$ solution of plasmid DNA encoding EYFP in modified patch clamp electrode buffer (148 mM KCl, 1 mM MgCl 2, 5 mM EGTA, 5 mM HEPES, 2 mM creatine, 5 mM phosphocreatine (sodium salt), 5×10$^{-3}$M ATP (dipotassium), pH 7.2) was prepared. Transfection was conducted using the custom stage in a tissue culture incubator for 2 hrs; after which the cells were trypsinized and transferred to a six-well tissue culture plate and cultured for 48 h. Expression of EYFP transfected cells was monitored by fluorescence microscopy before transfection, and every 24 hrs after transfection for 2 days. Cells were then trypsinized and collected in 100 μL of CSFM for flow cytometry.

DNA transfection was conducted via lipofection for comparison. HEK293 cells were seeded and cultured on a well of 24-well tissue culture plate for 48 hrs. Lipofection was performed using commercial reagents and protocols (Polyplus Transfection, jetPRIME). In brief, 0.5 μg of plasmid DNA was added into 50 μL of jetPRIME buffer. After mixing, 1.3 μL of jetPRIME reagent was added to the mixture and vortexed for 10 s. The final mixture was incubated at room temperature for 10 min, and then added to 0.5 mL of growth medium of the cells. The cells were incubated in the lipofection solution overnight. Cells were then trypsinized and collected in 100 μL of CSFM for flow cytometry. FIG. 16 illustrates the flow cytometry results of the lipofected cells, indicating that 90.8% of the cells were transfected.

Flow Cytometry:

Flow cytometry was utilized to quantify transfection efficiency from a large population of cells. Analysis was carried out on a BD Biosciences Accuri C6 Flow Cytometer, using 488 excitation/670 nm emission to detect PI fluorescence, and 488 nm excitation/530 nm emission to detect calcein-AM and EYFP fluorescence. A cut-off percentage of 0.2% (PI) or 0.1% (EYFP) positive within the control untransfected sample was used to set the gates. Side scatter (SSC) data were also collected and plotted on the Y-axis versus fluorescence intensity on X-axis. Transfection efficiency was reported as the ratio of the number of transfected live cells to the number of live cells.

Scanning Electron Microscopy:

Following culture on CNT array device for 48 hrs, L6 cells were fixed in 3% glutaraldehyde/0.1% sodium phosphate pH 7.4 for 30 min at room temperature, washed twice with PBS for 5 min, and then dehydrated in a graded ethanol series at room temperature, first for 10 min in 30% ethanol/PBS, and then successively in 50%, 70%, 85%, 95%, and 100% ethanol. CNT devices with fixed and dehydrated cells were then further dried in a critical point dryer (Tousimis PVT-3B), and coated with platinum in a DC sputter coater (Denton Vacuum DESK-II). The cells were examined using a field emission scanning electron microscope (Zeiss Auriga).

The CNT array device is well tolerated by cells, which adhere and grow with characteristics similar to tissue culture plastic, indicating applications for cells that are resistant to current transfection protocols such as macrophages, primary neurons, and stem cells. Additionally, gene transfer by CNT array is not associated with cell distress, and has significantly fewer side effects on cellular physiology than standard transfection methods, speeding development of new cell models to study intractable diseases, discovery of signaling pathways, and drug discovery.

The CNT array and CNT transfer system according to the present invention, present an easy-to-use, low cost means for supporting cell growth and facilitate transfer of agents 700 into target cells by combining high-throughput, high-efficiency, and high cell viability with low cytotoxicity. The technologies of the present invention also enable transfer of larger quantities of test substances into cell populations of greater variety, within a short period of time.

The CNT technology of the present invention facilitates the transfer of agents into difficult-to-transfect cells, which will have immediate impact on studies using primary cells, embryonic stem cells, and immortalized cell lines; as well as long-term impact on in vivo applications, such as gene therapy and drug delivery. In particular, the CNT technologies of the present invention can inject cell impermeable molecules, such as macromolecules, genetic material, and nanoparticles, into cells cultured directly on its surface. Generally, such agents are unable to bypass cell plasma membrane without a transport technique or reagent. As such, the CNT technologies of the present invention may render conventional transfection methods obsolete.

The CNT technologies of the present invention facilitate the removal of target cells from the CNT array without rupturing the cell membrane, or without compromising the integrity of the cell membrane. In this way, the present invention enables the transfer of agents into target cells while retaining the cells in a manner that facilitates their subsequent removal for further culturing and/or additional post-injection applications.

Those skilled in the relevant arts will appreciate the CNT technologies of the present invention can not only generate new insights into fundamental cell physiology by in situ cytosolic delivery, imaging and monitoring of various species; but also provide a standardized platform that facilitates the transfer of biomolecules into difficult-to-transfect cells, which will have immediate impact on primary cell culture, and long-term impact on in vivo applications such as gene therapy or drug delivery.

It will also be appreciated that the use of carbon in constructing the CNTs in the inventive CNT technologies provides the technologies with conductive nanotubes enable the CNT technologies to incorporate electrical detection and electrochemical sensing functionalities; thereby enabling the merging of several powerful diagnostic techniques to gather highly resolved and integrated quantitative data from many cells at once; and, thus, can provide a platform for various biological and biomedical applications including facilitating data collection in various cellular studies; infection of cells that are difficult to infect such as macrophages; and synchronizing cell proliferation through injection of proper messengers.

The inventive CNT technologies may also provide a cost effective means to manufacture implantable sensors with diagnostic capabilities and the functionality to simultaneously transport fluids and signal detection for therapeutic purposes. Applications of the inventive CNT technology may advance the study of single cells as a means of expediting and advancing biomedical research, including fundamental cell physiology, drug development and treatment efficacy, and point-of-care diagnostics; and could lead to wearable or implantable intracellular electrochemical devices for in situ monitoring and personalized medicine.

Although the present invention is described with reference to particular embodiments, it will be understood to those skilled in the art that the foregoing disclosure addresses exemplary embodiments only; that the scope of the invention is not limited to the disclosed embodiments; and that the scope of the invention may encompass additional embodiments embracing various changes and modifications relative to the examples disclosed herein without departing from the scope of the invention as defined in the appended claims and equivalents thereto.

While the disclosed methods may be performed by executing all of the disclosed steps in the precise order disclosed, without any intermediate steps there between, those skilled in the art will appreciate that the methods may also be performed: with further steps interposed between the disclosed steps; with the disclosed steps performed in an order other than the exact order disclosed; with one or more disclosed steps performed simultaneously; and with one or more disclosed steps omitted. For example, CNT array construction may be performed via a selective carbon CVD process (e.g., such as one employing a mask layer during the CVD process) whereby the CVD process step selectively deposits carbon only within the pores of the template substrate without depositing any appreciable quantity of carbon on the planar surface of the template substrate. In such a process, the CVD process step (e.g., step S20) may yield a carbon-lined substrate and the step of etching a carbon-coated substrate to remove a carbon-coating on the top surface of the substrate (e.g., step S30) may be omitted, and the process may instead proceed directly to the step of selectively etching the template substrate material for exposing the deposited carbon-linings with the pores (e.g., step S40). Also, the carbon deposition step (e.g., step S20) may include various types of CVD processes including thermal CVD, low pressure CVD, plasma enhanced CVD or catalytic CVD.

To the extent necessary to understand or complete the disclosure of the present invention, all publications, patents, and patent applications mentioned herein are expressly incorporated by reference herein to the same extent as though each were individually so incorporated. Ranges expressed in the disclosure include the endpoints of each range, all values in between the endpoints, and all intermediate ranges subsumed by the endpoints.

The present invention is not limited to the exemplary embodiments illustrated herein, but is instead characterized by the appended claims.

What is claimed is:

1. A carbon nanotube (CNT) array, comprising:
hollow carbon nanotubes arranged on a base;
wherein the base comprises a first planar surface and a second planar surface;
wherein the hollow carbon nanotubes extend from the first planar surface to the second planar surface, and comprise first open ports at the first planar surface and second open ports at the second planar surface;
wherein the first open ports are inlet ports and the second open ports are outlet ports, and a fluid flow passage channel extends between pairs of inlet and outlet ports such that there is a fluidic communication between the first planar surface and the second planar surface of the base via the hollow carbon nanotubes;
wherein the hollow carbon nanotubes comprise nanotubes having a diameter of from at least about 160 nm to at least about 250 nm;
wherein the hollow carbon nanotubes comprise nanotubes arranged with about 350 nm to about 450 nm center-to-center spacing;
wherein substantially all nanotubes in the CNT array extend no further than about 450 nm beyond the second planar surface of the base; and
wherein the hollow carbon nanotubes have a configuration that enables support of a cell thereon without compromising the cell membrane.

2. The CNT array of claim 1, wherein the base comprises anodized aluminum oxide.

3. The CNT array of claim 1, wherein the hollow carbon nanotubes are coated with a representation of the extracellular matrix.

4. The CNT array of claim 3, wherein the representation of the extracellular matrix is a hydrogel, laminin, fibronectin, or poly-lysine.

5. CNT transfer system, comprising:
a CNT array according to claim 1; and
an administration platform;
wherein the administration platform comprises an open end and a closed end, the open end having an opening dimensioned to accommodate placement of the CNT array inside the administration platform; and
wherein the administration platform comprises one or more support surfaces for supporting the CNT array and preventing the CNT array from contacting the closed end.

6. A CNT transfer system, comprising:
a CNT array according to claim 1; and
an administration platform;
wherein the administration platform comprises two open ends, with at least a first of the two open ends being dimensioned to accommodate placement of the CNT array inside the administration platform;
wherein the second of the two open ends has a perimeter edge suitable for being sealably engaged with a planar surface of a tissue culture dish; and
wherein the administration platform comprises one or more support surfaces that for supporting the CNT array and preventing the CNT array from contacting the planar surface of the tissue culture dish.

7. A CNT transfer kit for administering an agent into a cell, comprising:
a CNT array according to claim 1; and
a culture platform.

8. The CNT kit of claim 7, further comprising a buffer.

9. The CNT kit of claim 8, wherein the buffer comprises one or more members selected from the group of Phosphate-buffered saline (PBS), serum-free media, and a buffer compatible with cytoplasmic physiology.

10. The CNT kit of claim 9, wherein the buffer further comprises an energy source.

11. The CNT kit of claim 10, wherein the energy source comprises at least one member selected from the group of ATP and phosphocreatine.

12. The CNT kit of claim 8, wherein the buffer consists essentially of an energy source, wherein the energy source consists of at least one member selected from the group of ATP and phosphocreatine.

13. A method of administering an agent into a cell with a carbon nanotube (CNT) array, comprising:
contacting the cell with a CNT array according to claim 1;
wherein the cell is placed in contact with the second planar surface of the base of the CNT array;
wherein the CNT array supports the cell without compromising the cell membrane; and
wherein the agent is administered to the first planar surface of the base in a manner allowing flow of the agent into the inlet ports, through the fluid passage channels, and out the outlet ports of the CNT array so as to come into contact with the cell supported on the CNT array.

14. The method of claim 13, wherein the agent is administered for a duration of between 30 min to 12 hours.

15. The method of claim 14, wherein the agent is administered for a maximum duration of 2 hours.

16. The method of claim 13, wherein the agent is administered 1, 2, or 3 times in a 24 hour period.

17. The method of claim 13, wherein the agent is a dye; nanostructures (particles, rods, tubes), vesicles; micelles; RNA; DNA; peptides; proteins; carbohydrates; and small molecules.

18. The method of claim 13, wherein the flow of the agent into the inlet ports is by a pressure, electrical, magnetic force, or concentration gradient.

19. The method of claim 18, wherein the flow of the agent into the inlet ports is by a pressure force.

20. The method of claim 19, wherein the flow of the agent into the inlet ports is by a magnetic force.

21. The CNT array of claim 1, wherein the hollow carbon nanotubes have an ordered configuration.

* * * * *